United States Patent [19]
McDonald et al.

[11] Patent Number: 5,189,179
[45] Date of Patent: Feb. 23, 1993

[54] SEROTONIN 5HT$_{1A}$ AGONISTS

[75] Inventors: Ian A. McDonald, Loveland; Ronald C. Bernotas, Cincinnati; Mark W. Dudley, Somerville; Jeffrey S. Sprouse, Cincinnati, all of Ohio

[73] Assignee: Merrell Dow Pharmaceuticals Inc., Cincinnati, Ohio

[21] Appl. No.: 735,700

[22] Filed: Jul. 30, 1991

Related U.S. Application Data

[63] Continuation-in-part of Ser. No. 574,710, Aug. 29, 1990, abandoned.

[51] Int. Cl.$^5$ ............... C07D 209/20; A61K 31/405
[52] U.S. Cl. ................................ 548/495; 548/496
[58] Field of Search ............... 548/495, 496; 514/415, 514/419

[56] References Cited

U.S. PATENT DOCUMENTS 2,725,386  11/1955  Bovet et al. .................. 260/340.3

FOREIGN PATENT DOCUMENTS 0054304  12/1981  European Pat. Off. .
0252005  6/1987   European Pat. Off. .

OTHER PUBLICATIONS

Marinus O. den Boer, et al., *Br. J. Pharmacol* (1991), 102, pp. 323–330, Role of 5HT$_1$-like receptors in the reduction of porcine cranial arteriovenous anastomotic shunting by sumatriptan.

Saxena, et al., *TiPS*, May 1989, vol. 10, pp. 200–204; 5HT$_1$-like receptor agonists and the pathophysiology of migraine.

Hamel et al., *Br. J. Pharmacol*, (1991), 102, pp. 227–233; Contractile 5HT$_1$ receptors in human isolated pial arterioles: correlation with 5-HT$_{1D}$ binding sites.

Edward E. Schweizer, et al.; *Psychopharmacology Bulletin*, vol. 22, No. 1, 1986, pp. 183–185; Open Trial of Buspirone in the Treatment of Major Depressive Disorder.

*European Journal of Pharmacology*, 180 (1990) pp. 339–349, Dreteler, et al.; Comparison of the cardiovascular effects of the 5-HT1A receptor agonist flexinoxan with that of 8-OH-DPAT in the rat.

*European Journal of Pharmacology*, 182 (1990) 63–72, Connor, et al.; Cardiovascular effects of 5HT$_{1a}$ receptor agonists injected into the dorsal raphe nucleus of conscious rats.

*Clinical Neuropharmacology*, vol. 14, No. 3, pp. 245–250, Julio Pascual, et al.; An open trial of Buspirone in Migraine Prophylaxis. Preliminary Report. (1991).

*European Journal of Pharmacology*, 163, (1989) 133–136, Peroutka, et al.; Sumatriptan (GR 43175) interacts selectively with 5-HT$_{1B}$ and 5-HT$_{1D}$ binding sites.

*Primary Examiner*—David B. Springer
*Attorney, Agent, or Firm*—J. Michael Dixon

[57] ABSTRACT

The present invention is directed to a new class of serotonin 5HT$_{1A}$ agonists.

25 Claims, No Drawings

SEROTONIN 5HT$_{1A}$ AGONISTS

This is a continuation in part of Ser. No. 07/574,710, filed Aug. 29, 1990, now abandoned.

The present invention is directed to a new class of serotonin 5HT$_{1A}$ and 5HT$_{1D}$ agonists, their use in the treatment of anxiety, depression, migraine, stroke and hypertension as well as pharmaceutical and diagnostic compositions containing them.

In accordance with the present invention, a new class of serotonin 5HT$_{1A}$ and $_{1D}$ agonists have been discovered which can be described by the following formula:

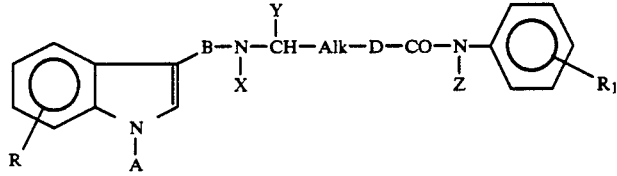

FORMULA Ia

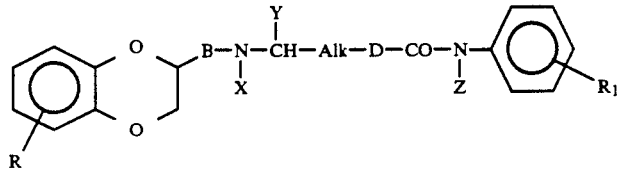

FORMULA Ib

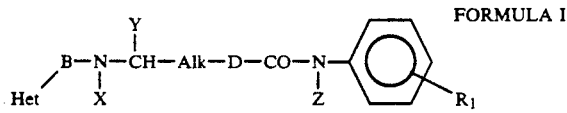

FORMULA I in which B is represented by a C$_{1-4}$ alkylene bridging group; Alk is represented by a linear alkylene bridging group containing from 2-8 carbon atoms which may optionally be mono-substituted at one carbon atom with a C$_{1-4}$ alkyl, phenyl, substituted phenyl or an alkylphenyl substituent in which the phenyl ring may be optionally substituted; D is represented by a bond or an ethenylene bridging group; X, Y, and Z are each independently represented by hydrogen, C$_{1-4}$ alkyl, phenyl, substituted phenyl or alkylphenyl in which the phenyl ring may be Optionally substituted; R$_1$ is represented by a substituent selected from the group consisting of hydrogen, halogen, C$_{1-4}$ alkyl, C$_{1-5}$ alkoxy, CF$_3$, OCF$_3$, OH, NO$_2$, CN, —CONR$_2$R$_3$, —NR$_2$R$_3$, —COOR$_4$, —OCH$_2$COOR$_4$, —CH$_2$SO$_2$NR$_2$R$_3$, and —SO$_2$NR$_2$R$_3$; R$_2$ and R$_3$ are each independently represented by H or a C$_{1-4}$ alkyl; R$_4$ is represented by H, C$_{1-4}$ alkyl, phenyl, substituted phenyl or an alkylphenyl substituent in which the phenyl ring may be optionally substituted; Het is represented by one of the following substituents:

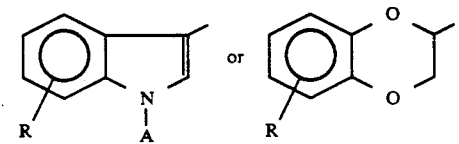

in which R is represented by a substituent selected from the group consisting of hydrogen, halogen, C$_{1-4}$ alkyl, C$_{1-4}$ alkoxy, O—CH$_2$—C$_6$H$_5$, CF$_3$, OCF$_3$, OH, NO$_2$, CN, —CONR$_5$R$_6$, —CH$_2$SO$_2$NR$_5$R$_6$, —SO$_2$NR$_5$R$_6$, —COOR$_7$ or —OCH$_2$COOR$_7$; R$_5$ and R$_6$ are each independently represented by H or C$_{1-4}$ alkyl; R$_7$ is represented by H, C$_{1-4}$ alkyl, phenyl, substituted phenyl or an alkylphenyl substituent in which the phenyl ring may be optionally substituted; A is represented by H, or C$_{1-4}$ alkyl; or a pharmaceutically acceptable salt thereof; with the proviso that when Het is an indolyl derivative, then R$_1$ is not a carbonyl derivative.

The compounds encompassed by Formula I above may also be represented by the following subgeneric formulae: in which R, A, B, Alk, D, X,Y, Z, and R$_1$ are as defined above.

These compounds mimic the effects of serotonin at the 5HT$_{1A}$ and $_{1D}$ receptor. They are useful in the treatment of anxiety, depression, migraine, stroke and hypertension.

As used in this application:

a) the term "halogen" refers to a fluorine, chlorine, or bromine atom;

b) the terms "lower alkyl group and C$_{1-4}$ alkyl" refer to a branched or straight chained alkyl group containing from 1-4 carbon atoms, such as methyl, ethyl, n-propyl, isopropyl, n-butyl, isobutyl, etc.;

c) the terms "lower alkoxy group and C$_{1-4}$ alkoxy" refer to a straight or branched alkoxy group containing from 1-4 carbon atoms, such as methoxy, ethoxy, n-propoxy, isopropoxy, n-butoxy, isobutoxy, etc.;

d) the term "substituted phenyl ring" refers to a phenyl moiety (C$_6$H$_5$) which is substituted with up to 3 substituents, each substituent is independently selected from the group consisting of halogens, C$_{1-4}$ alkyl, C$_{1-4}$ alkoxy, CF$_3$, OCF$_3$, OH, CN, and NO$_2$. These substituents may be the same or different and may be located at any of the ortho, meta, or para positions.

e) the term "alkylphenyl substituent" refers to the following structure, —(CH$_2$)$_m$—C$_6$H$_5$, in which m is an integer from 1-3. This phenyl ring may be substituted in the manner described immediately above.

f) the term "pharmaceutically acceptable salt" refers to either a basic addition salt or an acid addition salt.

g) the phrase "C$_{1-4}$ alkylene bridging group" refers to a methylene, ethylene, propylene, butylene, 1-methylethylene, 2-methyl-ethylene, 2-methyl-propylene, 2-ethyl-ethylene, 1-ethyl-ethylene, etc.

h) the term "ethenylene bridging group" refers to the following substituent:—CH=CH—.

i) the term "Alk" refers to a linear alkylene group which may be represented by the following structure:

—$(CH_2)_p$—CHL—$(CH_2)_s$, in which p and s are each independently represented by an integer from 0–7 and L is represented by H, $C_{1-4}$ alkyl, phenyl, substituted phenyl or an alkylphenyl substituent in which the phenyl ring may be optionally substituted, with the proviso that the sum p and s is from 1–7. Representative examples of such linear alkylene groups include ethylene, propylene, butylene, hexylene, δ-benzylpentylene, β-ethyl-heptylene, α-phenyl-propylene, β-benzylpentylene, α-methylpentylene, α-methylbutylene, etc. For the purposes of this application, the α-carbon should be considered to be the carbon atom immediately adjacent to the carbon atom bearing the Y-substituent.

j) the term "indolyl derivative" refers to a compound in which Het is represented by:

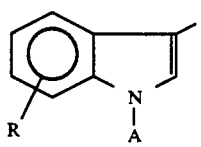

k) the term "benzodioxan" derivative refers to a compound in which Het is represented by:

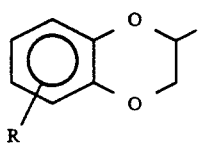

l) the term carbonyl derivative refers to one of the following substituents: —$CONR_2R_3$, —$COOR_4$, —$OCH_2COOR_4$, —$CONR_5R_6$, —$COOR_7$, —$OCH_2COOR_7$.

m) the term $C_{1-5}$ alkoxy refers to: a straight or branched alkoxy group containing from 1–5 carbon atoms, such as methoxy, ethoxy, n-propoxy, isopropoxy, n-butoxy, isobutoxy, n-pentoxy, etc.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methanesulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Some of the compounds of Formula I contain one or more asymmetric centers and will therefore exist as enantiomers and diastereomers. Any reference in this application to one of the compounds represented by Formula I, or any intermediate thereof, should be construed as covering a specific optical isomer, a racemic mixture or a diastereomeric mixture. The specific optical isomers can be synthesized or can be separated and recovered by techniques known in the art such as chromatography on chiral stationary phases, resolution via chiral salt formation and subsequent separation by selective crystallization, or enzymatic hydrolysis using stereoselective esterases as is known in the art. Alternatively, a chirally pure starting material may be utilized.

Those compounds of Formula I in which D is an ethenylene bridging group will also exist as geometric isomers. Any reference to these compounds should be construed as referring to either the cis isomer, the trans isomer or a mixture of these isomers.

All of the compounds of Formula Ia contain an indole. This indole may be optionally substituted as is indicated by the presence of the R substituent. When R is represented by a substituent other than hydrogen, there can be up to 3 such non-hydrogen substituents occurring on the indole ring. These substituents may appear at any of positions 2, 4, 5, 6, or 7. The 1-position of the indole may also be optionally substituted as indicated by the A substituent.

All of the compounds represented by Formula Ib contain a benzodioxan. This benzodioxan may be optionally substituted as indicated by the R substituent. When R is represented by a substituent other than hydrogen, there can be up to 3 such non-hydrogen substituents occurring on the benzodioxan. These substituents may be located at any of positions 3, 5, 6, 7 or 8.

All of the compounds of Formula I contain a phenyl ring adjacent to the amide substituent. This phenyl ring may also be substituted as is indicated by the $R_1$ substituent. When $R_1$ is represented by a substituent other than hydrogen, there can be up to 3 such non-hydrogen substituents occurring on the phenyl ring. These substituents can be the same or different and can be located at any of the ortho, meta, or para positions. As noted above, if Het is represented by an indolyl derivative, then $R_1$ should not be represented by a carbonyl derivative.

The amino-alkylene chain connecting the benzodioxan or indole with the terminal phenyl ring may be further substituted as indicated by the X, Y, and Z substituents. X, Y, and Z may be represented by the same substituents or differing substituents. As noted above, Alk is represented by a linear alkylene group. This alkylene group may be further substituted with only one alkyl, phenyl or alkylphenyl substituent. This one substituent may occur on any one carbon atom of the alkylene chain.

Examples of compounds encompassed by the present invention include:

a) 6-[[2-(5-hydroxy-1H-indol-3-yl)ethyl]amino]-N-[4-(trifluoromethyl)phenyl]-heptanamide;

b) 7-[[2-(5-hydroxy-1H-indol-3-yl)ethyl]amino]-N-(4-methoxyphenyl)-octanamide;
c) 6-[[2-(5-hydroxy-1H-indol-3-yl)ethyl]amino]-N-phenylheptanamide;
d) 5-[[2-(5-hydroxy-1H-indol-3-yl)ethyl]amino]-N-[4-(trifluoromethyl)phenyl]-hexanamide;
e) 6-[[2-(5-hydroxy-1H-indol-3-yl)ethyl]amino]-N-(4-methoxyphenyl)-heptanamide;
f) 4-[[2-(5-hydroxy-1H-indol-3-yl)ethyl]amino]-N-[4-(trifluoromethyl)phenyl]-pentanamide;
g) 6-[[2-(5-methoxy-1H-indol-3-yl)ethyl]amino]-N-[4-(trifluoromethyl)phenyl]-heptanamide;
h) 6-[[2-(5-hydroxy-1H-indol-3-yl)ethyl]methylamino]-N-[4-(trifluoromethyl)phenyl]-heptanamide;
i) 6-[[2-(5-hydroxy-1H-indol-3-yl)ethyl]amino]-N-(2-methoxyphenyl)-heptanamide;
j) 6-[[2-(5-carboxamido-1H-indol-3-yl)ethyl]amino]-N-(4-methoxyphenyl)-heptanamide;
k) 6-[[2-(1H-indol-3-yl)ethyl]amino]-N-[4-(trifluoromethyl)phenyl]-hexanamide;
l) 6-[[2-(5-hydroxy-1H-indol-3-yl)ethyl]amino]-N-[4-(1-propyl)phenyl]-hexanamide;
m) 5-[[2-(5-hydroxy-1H-indol-3-yl)ethyl]amino]-N-[4-(1-propyloxy)phenyl]-hexanamide;
n) 6-[2-[(2,3-dihydro-1,4-benzodioxin-2-yl)ethyl]amino]-N-phenyl-hexanamide;
o) 6-[(2,3-dihydro-1,4-benzodioxin-2-yl)methylamino]-N-[4-(trifluoromethyl)phenyl]-heptanamide;
p) 6-[(2,3-dihydro-1,4-benzodioxin-2-yl)methylamino]-N-(4-methoxyphenyl)-heptanamide;
q) 6-[[(2,3-dihydro-1,4-benzodioxin-2-yl)methyl]methylamino]-N-[4-(trifluoromethyl)phenyl]-hexanamide;
r) 6-[(2,3-dihydro-1,4-benzodioxin-2-yl)methylamino]-N-[2-(trifluoromethyl)phenyl]-hexanamide;
s) 7-[[2-(5-hydroxy-1H-indol-3-yl)ethyl]amino]-N-(4-methoxyphenyyl)-heptanamide;
t) 7-[[2-(5-hydroxy-1H-indol-3-yl)ethyl]amino]-N-(2-methoxyphenyl)-heptanamide;
u) 6-[[2-(4-hydroxy-1H-indol-3-yl)ethyl]amino]-N-(4-methoxyphenyl)-heptanamide;
v) 6-[[2-(5-chloro-1H-indol-3-yl)ethyl]amino]-N-(4-methoxyphenyl)-heptanamide;
w) 7-[[2-(5-hydroxy-1H-indol-3-yl)ethyl]amino]-N-(3-methoxyphenyl)-octanamide;
x) 6-[[2-(5-hydroxy-1H-indol-3-yl)ethyl]amino]-N-[2-(trifluoromethyl)phenyl]-hexanamide;
y) 6-[[2-(5-hydroxy-1H-indol-3-yl)ethyl]amino]-N-[3-(trifluoromethyl)phenyl]-hexanamide;
z) 6-[[2-(5-hydroxy-1H-indol-3-yl)ethyl]amino]-4-methyl-N-(4-methoxyphenyl)-hexanamide;
aa) 6-[[3-(5-hydroxy-1H-indol-3-yl)propyl]amino]-N-(4-methoxyphenyl)-hexanamide;
bb) 6-[[2-(5-hydroxy-1H-indol-3-yl)ethyl]amino]-N-(3-methoxyphenyl)-hexanamide;
cc) 6-[[2-(5-hydroxy-1-methyl-indol-3-yl)ethyl]amino]-N-(4-methoxyphenyl)-hexanamide;
dd) 6-[(2,3-dihydro-8-methoxy-1,4-benzodioxin-2-yl)methylamino]-N-(4-methoxyphenyl)-hexanamide;
ee) 5-[(2,3-dihydro-1,4-benzodioxin-2-yl)methylamino]-N-[4-(trifluoromethyl)phenyl]-pentanamide;
ff) 4-[(2,3-dihydro-1,4-benzodioxin-2-yl)methylamino]-N-(4-methoxyphenyl)-butanamide;
gg) 7-[[2-(5-methoxy-1H-indol-3-yl)ethyl]methylamino]-N-(4-methoxyphenyl)-octanamide;
hh) 6-[[2-(5-hydroxy-1H-indol-3-yl)ethyl]amino]-N-(4-methoxyphenyl)-2-hexenamide.

ii) 7-[(2,3-Dihydro-1,4-benzodioxin-2-yl)methylamino]-N-[4-trifluoromethyl)phenyl]-heptanamide.

Examples of preferred $5HT_{1A}$ agonists include:
a) 5-[(2,3-Dihydro-1,4-benzodioxin-2-yl)methylamino]-N-[4-(trifluoromethyl)phenyl]-pentanamide;
b) 6-[(2,3-Dihydro-1,4-benzodioxin-2-yl)methylamino]-N-[2-(trifluoromethyl)phenyl]-hexanamide;
c) 6-[[2-(5-Hydroxy-1H-indol-3-yl)ethyl]amino]-N-[4-(trifluoromethyl)phenyl]-heptanamide;
d) 7-[[2-(5-Hydroxy-1H-indol-3-yl)ethyl]amino]-N-(4-methoxyphenyl)-octanamide;
e) 6-[[2-(5-Hydroxy-1H-indol-3-yl)ethyl]amino]-N-phenylheptanamide;
f) 5-[[2-(5-Hydroxy-1H-indol-3-yl)ethyl]amino]-N-[4-(trifluoromethyl)phenyl]-hexanamide;
g) 6-[[2-(5-Hydroxy-1H-indol-3-yl)ethyl]amino]-N-(4-methoxyphenyl)-heptanamide;
h) 6-[[2-(5-Hydroxy-1H-indol-3-yl)ethyl]amino]-N-[4-(trifluoromethyl)phenyl]-hexanamide;
i) 6-[[2-(5-Hydroxy-1H-indol-3-yl)ethyl]amino]-N-(3,4-dimethoxyphenyl)-heptanamide;
j) 6-[[2-(5-Hydroxy-1H-indol-3-yl)ethyl]amino]-N-(4-methoxyphenyl)-octanamide;
k) 4-[[2-(5-Hydroxy-1H-indol-3-yl)ethyl]amino]-N-[4-(trifluoromethyl)phenyl]-pentanamide;
l) 6-[[2-(5-Hydroxy-1H-indol-3-yl)ethyl]amino]-N-(2-methoxyphenyl)-heptanamide;
m) 5-[(2,3-dihydro-1,4-benzodioxin-2(S)-yl)methyl amino]-N-(4-chlorophenyl)-pentanamide;
n) 5-[(2,3-dihydro-1,4-benzodioxin-2-yl)methylamino]-N-(3,4-dichlorophenyl)-pentanamide;
o) 5-[(2,3-dihydro-1,4-benzodioxin-2-yl)methylamino]-N-(4-dimethylaminophenyl)-pentanamide;
p) 6-[(2,3-dihydro-1,4-benzodioxin-2-yl)methylamino]-N-(4-methoxyphenyl)-hexanamide;
q) 7-[2-[(5-hydroxy-1H-indol-3-yl)ethyl]amino]-N-phenylheptanamide.

Preferred $5HT_{1D}$ Agonists include:
a) 5-[(2,3-dihydro-1,4-benzodioxin-2-yl)methylamino]-N-[4-(trifluoromethyl)phenyl]-pentanamide;
b) 5-[(2,3-dihydro-1,4-benzodioxin-2(S)-yl)methylamino]-N-(4-chlorophenyl)-pentanamide;
c) 5-[(2,3-dihydro-1,4-benzodioxin-2(S)-yl)methyl amino]-N-[4-(trifluoromethyl)phenyl]-pentanamide;
d) 6-[[2-(5-hydroxy-1H-indol-3-yl)ethyl]amino]-N-[3-(trifluoromethyl)phenyl]-hexanamide;
e) 6-[[2-(5-Hydroxy-1H-indol-3-yl)ethyl]amino]-N-[4-(trifluoromethyl)phenyl]-hexanamide.

The compounds of Formula Ia can be prepared using techniques known in the art. One suitable method is disclosed below in Reaction Scheme I:

REACTION SCHEME I

STEP A

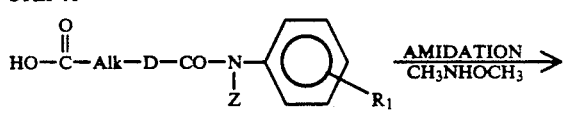

STEP B

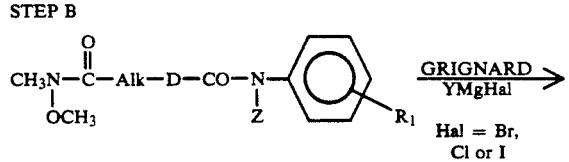

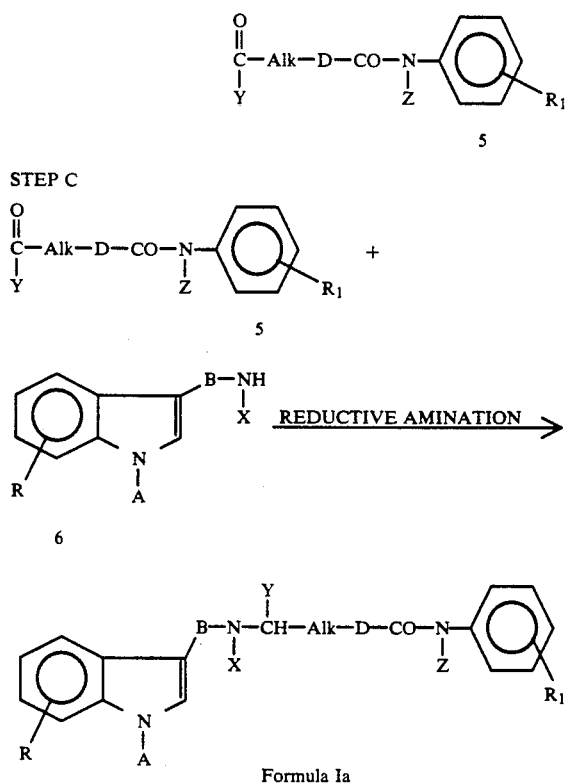

-continued
REACTION SCHEME I

STEP C

Formula Ia

As is depicted, the initial step in the reaction is to carry out an amidation reaction between the acid derivative of structure 1 and N,O-dimethylhydroxylamine, thereby producing the amido-derivative depicted by structure 3. This amido-derivative is subjected to a Grignard reaction thereby producing the compound of structure 5. The desired product of Formula Ia is then produced by carrying out a reductive amination between the compound of structure 5 and the indole derivative of structure 6.

The appropriate acid derivative to utilize as a starting material is One in which Alk, D, $R_1$, and Z are represented by the same substituents as is desired in the final product of Formula Ia. Methods for producing these acid derivatives are known in the art. For example, see Leznoff, C. C. and Goldwasser, J. M. *Tetrahedron Letters,* 1875–1878 (1977) and Leznoff C. C. and Goldwasser, J. M., *Can. J. Chem.,* 56, 1562–1568 (1978).

The amidation reaction of Step A can be carried out using techniques known in the art. Typically approximately equivalent amounts of the acid derivative and N,O-dimethylhydroxylamine are contacted in the presence of an approximately equivalent amount of a peptide coupling reagent such as isobutylchloroformate. The amidation is also typically carried out in the presence of an approximately equivalent amount of a base such as triethylamine, 4-ethylmorpholine, or 4-methylmorpholine. The reaction is typically carried out in an aprotic solvent such as tetrahydrofuran or dichloromethane for a period of time ranging from 1 to 24 hours. The reaction is typically carried out at a temperature range of from $-20°$ to 20° C.

The resulting amide derivative of structure 3 can be recovered from the reaction zone by extraction with dichloromethane. It may then be purified by recrystallization from a solvent system such as ethyl acetate/hexane. Alternatively, it may be purified by flash chromatography utilizing an eluting agent such as a mixture of ethyl acetate and hexane.

In Step B, this amide derivative is subjected to a Grignard reaction in which the Grignard reagent is as described by structure 4 in which Y is as in Formula Ia and is represented by the same substituent as is desired in the final product. Typically, the amide of structure 3 is contacted with an excess of the Grignard reagent (2.0 to 3.0 equivalents) in an ethereal solvent such as ether or tetrahydrofuran at $-78°$ C. The reaction is warmed to room temperature and stirred for 8 to 36 hours. The resulting ketone derivative of structure 5 can be recovered by extraction. It may then be purified by flash chromatography with an eluting agent such as a 50:50 mixture of ethyl acetate and hexane.

In Step C, a reductive amination is carried out between the ketone or aldehyde derivative of structure 5 and the indole derivative of structure 6 in which R, A, X, and B are as in Formula Ia and are represented by the same substituents as is desired in the final product. Several of these indoles are items of commerce and methods for producing other indole derivatives are known in the art. For example, see Lloyd, D. H., Nichols, *J. Org. Chem.* 51, 4294–4295 (1986); Naito, T. et al., *Synthesis,* 778–780 (1989); Webb, C., U.S. Pat. No. 4,252,803; Abramovitch, R. A., Shapiro, D., *J. Chem. Soc.* 4589 (1956); Demerson, C. A. et al;, *J. Med. Chem.* 31, 1344–50 (1988).

The reductive amination is carried out using techniques known in the art. Typically the hydrochloric acid or maleic acid salt of the indole derivative of structure 6 is contacted with an equivalent or a slight excess of the compound of structure 5. The reductive amination is carried out in the presence of an excess of sodium cyanoborohydride (about 1.5 equivalents). The reaction is typically carried out in an alcoholic solvent such as methanol at a concentration of 0.1 molar. The reaction is carried out at room temperature for a period of time ranging from 1 to 7 days. The resulting product of Formula Ia can be recovered by the addition of sodium bicarbonate and water followed by extraction with a 1:4 mixture of 2-propanol and dichloromethane. It may be purified by flash chromatography with an eluting system such as 5:20:80 triethylamine:ethanol:ethyl acetate.

Alternatively, the compounds of structure 5 can also be prepared according to the procedures described in *Journal of Medicinal Chemistry,* 26(4), 494 (1983) and in *Int. J. Pept. Protein Res.,* 22, 284 (1983).

Those compounds of structure 5 wherein Y=H can be made from the bromides of structure 8 (depicted below in Reaction Scheme II) by procedures known in the art. For example see Kornblum, N. et al., *J. Am. Chem. Soc.,* 81, 4113–4114 (1959) and Ganem, B., Boeckman, R. K., *Tetrahedron Letters,* 917–920 (1974). In a typical procedure, approximately equimolar amounts of bromides of structure 8 (where Y=H and Alk, D, Z, and $R_1$, are as required structure 5) and sodium bicarbonate are stirred in dimethylsulfoxide (0.1–0.3M) with a catalytic amount of potassium iodide. The mixture is typically heated under a nitrogen atmosphere at a temperature of from 100° to 150° C. for 2–10 hours. The resulting aldehyde derivative of structure 5 (Y=H) can be recovered by addition of water and extraction with diethyl ether. It may be purified by flash chromatography utilizing an eluant mixture such as 50:50 ethyl acetate:hexane.

The benzodioxan derivatives of Formula Ib can also be prepared by techniques known in the art. One suitable method is disclosed below in Reaction Scheme II:

REACTION SCHEME II

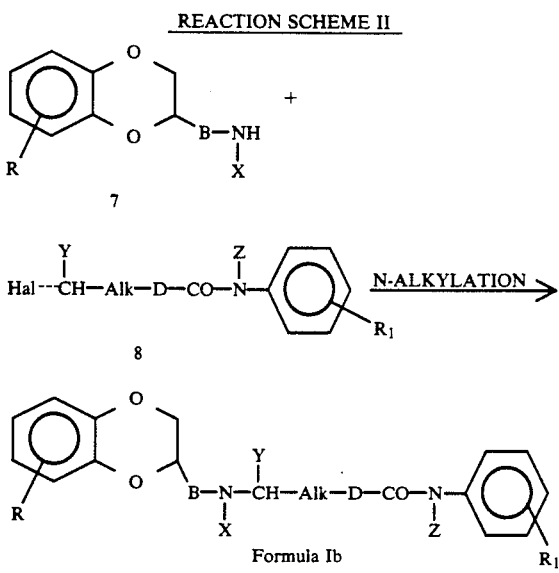

Formula Ib

As is depicted above, the compounds of Formula Ib are prepared by carrying out an N-alkylation between a benzodioxan derivative as described by structure 7 in which R, X and B are as in Formula Ib and an alkylhalide derivative as described by structure 8 in which Alk, D, $R_1$, Y and Z are as in Formula Ib and Hal is a halogen. The appropriate benzodioxan derivative to use is one in which R, X and B are represented by the same substituents as is desired in the final product. Methods for producing these benzodioxans are known in the art. For example, see Dewar, G. H. et al., *Eur. J. Med. Chem. Chim. Ther.* 18, 286–289 (1983); Shapero, M., et al., *J. Med. Chem.* 12, 326–329. The appropriate alkylhalide derivative of structure 8 to use is one in which Y, Z, Alk, D and $R_1$ are represented by the same substituents as is desired in the final product. Methods for producing the alkylhalide derivatives are known in the art. For example, see Stirling, C. J. M., *Journal of the Chemical Society*, 4531–4536 (1958), and Stirling, C. J. M., *Journal of the Chemical Society*, 255–262 (1960).

The N-alkylation reaction is carried out using techniques known in the art. Typically approximately equimolar amounts of the reactants are contacted in a polar, aprotic solvent such as dimethylformamide or dimethylsulfoxide. The reaction is usually carried out for a period of time ranging from 30 minutes to 8 hours at a temperature range of 50° to 100° C. The desired product of Formula Ib can be recovered by extraction after saturated aqueous sodium bicarbonate has been added to the reaction. It may then be purified by recrystallization from a solvent system such as ethanol:ethyl acetate and/or it may be purified by flash chromatography with an eluting agent such as 10:90 ethanol:ethyl acetate.

Alternatively, the compounds of Formula Ib can be prepared by the procedure outlined above in Reaction Scheme I. The only modification is that the benzodioxan derivative of structure 7 is utilized rather than the indole derivative of structure 6. Likewise, the compounds of Formula Ia in which R is H can be prepared by the method disclosed in Reaction Scheme II, but substituting the appropriate indole starting material for the benzodioxan of structure 7.

The compounds of Formula I are serotonin $5HT_{1A}$ agonists and are therefore useful in the treatment of anxiety, hypertension, and depression. The affinity of the compounds for the $5HT_{1A}$ receptor can be demonstrated by receptor binding assay procedures such as described by Gozlan et al. in *Nature*, Volume 305, at pages 140–142 (1983). The procedure of Sleight et al., as reported in the *European Journal of Pharmacology*, Volume 154, pages 255–261 (1988) can be utilized to show that this affinity results in an agonistic effect upon the receptor.

The compounds slow the firing of neurons in the dorsal raphe nucleus which contains one of the highest densities of $5HT_{1A}$ receptors in the CNS. Inhibition of cell firing results in a reduction in the amount of serotonin released in brain regions receiving input from the dorsal raphe, thereby altering serotonin tone in the system. A slowing of the firing rate can be demonstrated by applying the compounds to rodent brain slices containing the dorsal raphe and measuring the activity of individual neurons. This procedure has been described by Sprouse et al., in the *European Journal of Pharmacology*, Vol. 167, pp 375–383 (1989). Other $5HT_{1A}$ agonists such as buspirone have been shown to inhibit raphe cell firing, an effect apparently common to all members of this pharmacologic class (Vandermaelen et al., *European Journal of Pharmacology*, Vol. 129, pp 123–130 (1986)).

It has been reported that $5HT_{1A}$ agonists are effective in the treatment of depression. The $5HT_{1A}$ agonist, 8-hydroxy-2-(di-N-propylamino) tetralin (8-OH DPAT) was shown to be effective in rodent models for depression. *European Journal of Pharmacology*, Vol 144., pages 223–229 (1987), Ceroo et al. and *European Journal of Pharmacology*, Vol. 58, pages 53–59 (1988), Ceroo et al. Schweizer et al. reported that buspirone, a partial $5HT_{1A}$ agonist, was useful in the treatment of depression. *Pharmacology Bulletin*, Vol. 22, No. 1 (1986). Since the compounds of the instant invention are $5HT_{1A}$ agonists, they will be useful in the treatment of depression.

In order to exhibit an antidepressant effect, it is necessary that the compounds be administered to the patient in an effective amount. The dosage range at which these compounds exhibit this antidepressant effect can vary widely depending upon the severity of the patient's depression, the particular compound being administered, the route of administration, the co-administration of other therapeutic agents, and the presence of other underlying disease states. Typically, the compounds will be administered at a dosage range of from 0.5 mg/kg/day to about 100 mg/kg/day. Repetitive daily administration may be desirable and will vary with the conditions described above. However, the compounds are typically administered from 1 to 4 times daily.

The compounds of Formula I will elevate the patient's mood if they are suffering from depression and either relieve or alleviate the physical complaints which the patient is experiencing.

As noted above, the compounds of Formula I are serotonin $5HT_{1A}$ agonists. Compounds producing this effect at the $5HT_{1A}$ receptor have also been found to exhibit anxiolytic properties. *European Journal of Pharmocology*, Vol. 88, pages 137–138 (1983) Gloser et al. and *Drugs of the Future* Vol. 13 pages 429–439 (1988)

Glaseat. A 5HT$_{1A}$ partial agonist known as buspirone is currently being marketed as an anxiolytic agent. Since the compounds of the instant invention are are 5HT$_{1A}$ agonists, they will be useful in the treatment of anxiety.

It is also possible to demonstrate the anxiolytic activity of these compounds by their ability to block distress vocalizations in rat pups. This test is based upon the phenomenon that when a rat pup is removed from its litter, it will emit an ultrasonic vocalization. It was discovered that anxiolytic agents block these vocalizations. The testing method has been described by Gardner, C. R., Distress vocalization in rat pups: a simple screening method for anxiolytic drugs., *J. Pharmacol. Methods* 14:181–1879 (1985), and Insel et al., Rat pup ultrasonic isolation calls: Possible mediation by the benzodiazepine receptor complex, *Pharmacol. Biochem. Behav.*, 24: 1263–1267 (1986).

In order to exhibit this anxiolytic effect, it is necessary that the compounds be administered to the patient in an effective amount. The dosage range at which these compounds exhibit this anxiolytic effect can vary widely depending upon the severity of the patient's anxiety, the particular compound being administered, the route of administration, the co-administration of other therapeutic agents, and the presence of other underlying disease states. Typically, the compounds will be administered at a dosage range of from about 0.5 mg/kg/day to about 100 mg/kg/day. Repetitive daily administration may be desirable and will vary with the conditions described above. However, the compounds are typically administered from 1 to 4 times daily.

The compounds of Formula I exhibit a hypotensive effect and are therefore useful in the treatment of hypertension. Other 5HT$_{1A}$ agonists such as 8-OH-DPAT and flesinoxan have been shown to be effective for the treatment of hypertension in rodent models *European Journal of Pharmacology*, Vol. 180, pages 339–349 (1990) and *European Journal of Pharmacology*, Vol. 182, pages 63–72 (1990). It is also possible to demonstrate the antihypertensive effects of these compounds using rodent models such as the spontaneously hypertensive rat. In this model, vehicle is administered to the rat orally or intravenously and a baseline blood pressure is established. The test compound is then administered by the same route and the decrease in blood pressure is noted. The compounds of Formula I produce a hypotensive effect.

In order to produce an antihypertensive effect, it is necessary that the compounds be administered to the patient in an effective amount. The dosage range at which these compounds exhibit this hypotensive effect can vary widely depending upon the severity of the patient's hypertension, the particular compound being administered, the route of administration, the co-administration of other therapeutic agents, and the presence of other underlying disease states. Typically, the compounds will be administered at a dosage range of from about 0.5 mg/kg/day to about 100 mg/kg/day. Repetitive daily administration may be desirable and will vary with the conditions described above. However, the compounds are typically administered from 1 to 4 times daily.

The compounds of the present invention may be administered by a variety of routes. They are effective if administered orally. The compounds may also be administered parenterally (i.e. subcutaneously, intravenously, intramuscularly, or intraperitoneally).

As used in this application:

a) the term "patient" refers to warm blooded animals such as, for example, guinea pigs, mice, rats, cats, rabbits, dogs, monkeys, chimpanzees, and humans;

b) the term "treat" refers to the ability of the compounds to either relieve, alleviate, or slow the progression of the patient's disease.

c) the term "anxiety" refers to the unpleasant emotional state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension.

d) the term "depression" should be construed as encompassing those conditions which the medical profession have referred to as major depression, endogenous depression, psychotic depression, involutional depression, involutional melancholia, etc. These conditions are used to describe a condition in which patients typically experience intense sadness and despair, mental slowing, loss of concentration, pessimistic worry, despair, and agitation. The patients often experience physical complaints such as insomnia, anorexia, decreased energy, decreased libido, etc.

Serotonin 5HT$_{1A}$ agonists have also been shown to be useful in the treatment of stroke. It has been discovered that these compounds exhibit a neuroprotective effect and will either relieve or inhibit the CNS damage that typically accompanies a stroke. This neuroprotective effect is believed to be due to serotonin's inhibitory effect upon excitatory neurotransmission. For example, Bielenberg et al showed that the 5HT$_{1A}$ agonists 8-OH-DPAT, buspirone, gepirone, ipsapirone, and Bay R 1531 inhibited or decreased neuronal destruction in rodent models of stroke. *Stroke Supplement IV*, Volume 21, No. 12 (December, 1990). Since the compounds of Formula I are serotonin 5HT$_{1A}$ agonists, they will be useful in the treatment of stroke.

In order to exhibit this neuroprotective effect, it is necessary that the compounds be administered to the patient in an effective amount. The dosage range at which these compounds exhibit this effect can vary widely depending upon the severity of the patient's condition, the particular compound being administered, the route of administration, the co-administration of other therapeutic agents, and the presence of other underlying disease states. Typically, the compounds will be administered at a dosage range of from 0.01 mg/kg/day to about 100 mg/kg/day. Repetitive daily administration may be desirable and will vary with the conditions described above. However, the compounds are typically administered from 1 to 4 times daily or as a continuous intravenous infusion.

Stroke is a condition in which injury to the brain results due to either ischemic or hemorrhagic lesions. It is also commonly referred to as a cerebrovascular accident. The compounds of Formula I can be used to treat any of these conditions. As used herein, the phrase "treating stroke" refers to the ability of the compounds to either inhibit or decrease the CNS damage that typically accompanies a stroke.

As is readily apparent to those skilled in the art, the compounds of Formula I will not correct any CNS damage that has already occurred as the result of the cerebrovascular accident. The compounds should be administered at the initiation of the cerebrovascular accident, or soon thereafter, prior to the occurrence of extensive CNS damage.

The compounds of Formula I are also serotonin $5HT_{1D}$ agonists. The affinity of the compounds for the $5HT_{1D}$ site can be demonstrated in binding procedures such as those described by Peroutka et al in *European Journal of Pharmacology*, Vol. 163 at pages 133–166 (1989).

It has been reported that $5HT_{1D}$ agonists are effective in the treatment of migraine. The $5HT_{1D}$ agonist, sumatriptan, was shown to produce antimigraine-like effects in animal models and to terminate acute migraine attacks in early clinical trials. Peroutka et al, id.; Saxena et al, TIPS- Vol. 10, page 200, May 1989; and Hamel et al, Br. J. Pharmacol. (1991) 102,227-223. Since the compounds of Formula I are serotonin $5HT_{1D}$ agonists, they may be utilized to terminate migraine attacks.

Migraine attacks are associated with excessive dilation of the extracerebral cranial vasculature. Since serotonin $5HT_{1D}$ agonists constrict these vessels, it is currently believed that this is the mechanism by which they terminate migraine attacks. Saxena et al, id. The ability of the compounds of Formula I to produce constriction of these extracerebral cranial vessels can be demonstrated using the method of Boer et al, Br. J. Pharmacol. (1991), 102, 323-330.

In addition to terminating acute migraine attacks, the compounds can be administered on a prophylactic basis to prevent the occurrence of migraines. In order to produce these antimigraine effects, it is necessary that the compounds be administered to the patient in an effective amount. The dosage range at which these compounds exhibit these anti-migraine effects can vary widely depending upon the severity of the patient's migraine, the particular compound being administered, the route of administration, the co-administration of other therapeutic agents, and the presence of other underlying disease states. Typically, the compounds will be administered at a dosage range of from about 0.5 mg/kg/day to about 100 mg/kg/day. Repetitive daily administration may be desirable and will vary with the conditions described above. However, the compounds are typically administered from 1 to 4 times daily.

Pharmaceutical compositions can be manufactured utilizing techniques known in the art. Typically an antidepressant, anxiolytic, anti-hypertenisve, anti-stroke, or anti-migraine amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The compounds of Formula I may also be admixed with any inert carrier and utilized in laboratory assays in order to determine the concentration of the compounds within the serum, urine, etc., of the patient as is known in the art.

The following Examples are being presented in order to further illustrate the invention, but they should not be construed as limiting the scope of the invention in any manner.

EXAMPLES

Example 1

6-[[2-(5-Hydroxy-1H-indol-3-yl)ethyl]amino]-N-[4-(trifluoromethyl)phenyl]-heptanamide, monohydrochloride, hemihydrate Serotonin hydrochloride hemihydrate (200 mg) and N-[4-(trifluoromethyl)phenyl]-6-oxo-heptanamide (260 mg) were dissolved in methanol (8 mL) and treated with sodium cyanoborohydride (85 mg). After stirring for 45 hours in the dark at 23° C., sodium bicarbonate (250 mg) and water (20 mL) were added and the reaction stirred 1 hour. The mixture was extracted with 1:4 2-propanol:dichloromethane (2×50 mL) and the combined extracts dried over $Na_2SO_4$ and concentrated in vacuo to an oil. This oil was chromatographed using 5:10:90, then 2.5:50:50 triethylamine:ethanol:ethyl acetate as eluant, and the component with an $R_f$ of 0.4 in the later solvent system was isolated as a slightly red, clear oil. This oil was reconcentrated from methanol (50 mL) three times, then dissolved in ethanol (50 mL) and treated with 1:9 concentrated hydrochloric acid:ethanol (1.1 mL). This solution was concentrated in vacuo and then reconcentrated first from 1:1 ethanol:methanol (50 mL), then from 1:4 methanol:ethyl acetate (50 mL). The title compound was obtained as a tan solid (370 mg).

Analysis calculated for $C_{24}H_{28}F_3N_3O_2 \cdot HCl \cdot 0.75 H_2O \cdot 0.05 CH_3CH_2OCOCH_3$: C, 57.92; H, 6.21; N, 8.37. Found: C, 57.91; H, 6.22; N, 8.27.

IR(KBr): 3302, 1604, 1534, 1410, 1326, 1164, 1114, 1068 $cm^{-1}$.

CIMS ($CH_4$): 448 (100%), 428 (40%), 219 (28%).

$^1H$ NMR ($d_6$-DMSO): 10.68 (1H, d; J=2.1 Hz), 10.01 (1H, s), 8.92 (2H, bm), 8.73 (1H, s), 7.86 (2H, d; J=9.0 Hz), 7.64 (2H, d; J=8.9 Hz), 7.16 (2H, m), 6.88 (1H, d; J=2.0 Hz), 6.63 (1H, dd; J=2.0, 8.4 Hz), 3.27-2.95 (5H), 2.42 (2H, t; J=7.5 Hz), 1.82 (1H, m), 1.67-1.20 (5H), 1.24 (3H, d; J=6.6 Hz) ppm.

$^{13}C$ NMR ($d_6$-DMSO): 171.83, 150.40, 142.94, 130.76, 127.49, 126.23, 125.95, 123.58, 122.90 (m), 118.84, 111.83, 111.57, 108.50, 102.07, 53.04, 44.16, 36.10, 31.93, 24.58, 24.37, 22.02, 15.56 Ppm.

$^{19}F$ NMR ($d_6$-DMSO): −60.098 ppm.

Example 2

2A) 7-Oxo-N-(4-methoxyphenyl)-octanamide

Prepared as in *J. Med. Chem.* 26, 492–499 (1983), Method C, except substituting p-anisidine for para-(n-butyl)-aniline. Recrystallized from hot ethyl acetate by the addition of 20:80 ethyl acetate:hexanes. The title compound was isolated as a pale violet solid.

Anal. Calc. for $C_{15}H_{21}NO_3$: C, 68.42; H, 8.04; N, 5.32. Found: C, 68.57; H, 8.22; N, 5.32.

IR(KBr): 3312, 2942, 1708, 1658, 1598, 1528, 1514, 1410, 1364, 1296, 1240, 823 cm$^{-1}$.

CIMS(CH$_4$): 264 (100%, M+H$^+$)

$^1$H NMR(CDCl$_3$): 7.76 (1H, bs), 7.43 (2H, d; J=9.0 Hz), 6.85 (2H, d; J=8.9 Hz), 3.78 (3H, s), 2.44 (2H, t; J=7.8 Hz), 2.31 (2H, t; J=7.3 Hz), 2.13 (3H, s), 1.70 (2H, m), 1.59 (2H, m), 1.35 (2H, m) ppm.

$^{13}$C NMR (CDCl$_3$): 210.13, 171.97, 156.81, 131.76, 122.21, 114.45, 55.66, 43.53, 37.20, 30.09, 28.68, 25.46, 23.33 ppm.

Melting point: 106.0°-107.0° C.

2B)

7-[[2-(5-Hydroxy-1H-indol-3-yl)ethyl]amino]-N-(4-methoxyphenyl)-octanamide, monohydrochloride Serotonin hydrochloride hemihydrate (222 mg), N-(4-methoxyphenyl)-7-oxo-octanamide (263.3 mg), and methanol (10 mL) were stirred in the dark and the resulting solution treated with sodium cyanoborohydride (95 mg). After 4 d at ca. 22° C., sodium bicarbonate (350 mg) and water (10 mL) were added. After stirring 1.5 hours, the mixture was extracted with 1:4 2-propanol:dichloromethane (3×25 mL) and the combined extracts were dried (Na$_2$SO$_4$) and concentrated in vacuo. Chromatography eluting with 4:10:90, then 3:30:70 triethylamine:ethanol:ethyl acetate gave a component with an R$_f$ of 0.3 in the latter solvent system. This oil was reconcentrated twice from ethanol (50 mL), then redissolved in ethanol (ca. 50 mL), treated with 1:9 concentrated hydrochloric acid:ethanol (1.2 mL), and reconcentrated in vacuo to a pale yellow oil which foamed to a solid. This was the title compound (352 mg), isolated as a pale yellow solid.

Analysis calculated for $C_{25}H_{33}N_3O_3.HCl.0.9\ H_2O.0.1\ CH_3CH_2OH$: C, 62.95; H, 7.63; N, 8.74. Found: C, 62.99; H, 7.58; N, 8.71.

IR(KBr): 3266, 2938, 1652, 1538, 1512, 1462, 1242 cm$^{-1}$.

CIMS (CH$_4$): 424 (100%), 277 (24%).

$^1$H NMR (d$_6$-DMSO): 10.68 (1H, d; J=2.0 Hz), 9.88 (1H, s), 8.92 (2H, bd), 7.53 (2H, d; J=9.0 Hz), 7.17-7.14 (2H), 6.87-6.83 (3H), 6.64 (1H, dd; J=2.2, 8.5 Hz); 3.71 (3H, s), 3.24-2.96 (5H), 2.29 (2H, t; J=7.2 Hz), 1.85-1.20 (8H), 1.24 (3H, d; J=6.5 Hz) ppm.

$^{13}$C NMR (d$_6$-DMSO): 170.65; 154.92, 150.37, 132.56, 130.74, 127.46, 123.53, 120.52, 113.70, 111.79, 111.54, 108.48, 102.04, 55.11, 53.17, 44.13, 36.04, 32.06, 28.33, 24.92, 24.51, 21.98, 15.52 ppm.

Example 3

3A) 6-Oxo-N-phenyl-heptanamide

Prepared as in *J. Med Chem.*, 26, 492–499 (1983), Method C, except substituting aniline for para-(n-butyl)-aniline. The title compound was purified by dissolving in hot ethyl acetate and adding hexane to give a white solid.

Anal. Calc. for $C_{13}H_{17}NO_2$: C, 71.21; H, 7.81; N, 6.39. Found: C, 70.94; H, 7.77; N, 6.21.

IR(KBr): 3340, 2945, 1706, 1664, 1599, 1534, 1447, 1375, 766, 695 cm$^{-1}$.

CIMS (CH$_4$): 220 (100%, M+H$^+$), 127 (67%).

$^1$H NMR (CDCl$_3$): 7.80 (1H, bs), 7.56 (2H, d; J=7.7 Hz), 7.31 (2H, app.t; J=7.8 Hz), 7.09 (1H, t; J=7.4 Hz), 2.50 (2H, t; J=6.5 Hz), 2.73 (2H, t; J=6.9 Hz), 2.15 (3H, s), 1.67 (4 H, m) ppm.

$^{13}$C NMR (CDCl$_3$): 209.20, 171.01, 138.02, 128.89, 124.09, 119.80, 43.21, 37.25, 29.99, 24.82, 22.97 ppm.

Melting point: 85.5°-86.5° C.

3B)

6-[[2-(5-Hydroxy-1H-indol-3-yl)ethyl]amino]-N-phenylheptanamide, monohydrochloride hydrate Serotonin hydrochloride (1.000 g) and N-phenyl-6-oxo-heptanamide (1.289 g) were stirred in methanol (47 mL) under a nitrogen atmosphere and treated with sodium cyanoborohydride (0.444 g), excluding light from the reaction. After 4 d at ca. 23° C., a solution of sodium bicarbonate (1.00 g) in water (25 mL) was added. One hour later, the reaction was diluted with water (75 mL) and extracted with 1:4 2-propanol:dichloromethane (3×75 mL). The combined extracts were dried (Na$_2$SO$_4$), filtered, and concentrated in vacuo to a foaming oil which was chromatographed using 5:20:80 triethylamine:ethanol:ethyl acetate, isolating the component with an R$_f$ of 0.3. The resulting oil was twice reconcentrated in vacuo from ethanol (100 mL) and then redissolved in ethanol (100 mL). This solution was treated with 1:9 concentrated hydrochloric acid: ethanol (6 mL), concentrated in vacuo, reconcentrated from ethanol (100 mL) to an oil, and the oil placed under vacuum to yield the title compound as a solid (1.80 g).

Anal. Calc. for $C_{23}H_{29}N_3O_2.HCl.1.2\ H_2O$: C, 63.13; H, 7.40; N, 9.60. Found: C, 63.37; H, 7.25; N, 9.57.

IR(KBr): 3404, 3274, 1660, 1598, 1542, 1442 cm$^{-1}$.

CIMS(CH$_4$): 380 (100%), 233 (20%).

$^1$H NMR (d$_6$-DMSO):10.70 (1H, d; J=2.0 Hz), 10.07 (1H, s), 8.95 (2H, bm), 8.75 (1H, bs), 7.63 (1H, d; J=7.5 Hz), 7.28 (2H, t; J=8.0 Hz), 7.17-7.14 (2H, m), 7.02 (1H, t; J=7.4 Hz), 6.88 (1H, d; J=2.1 Hz), 6.65 (1H, dd; J=2.2, 8.5 Hz), 3.48-3.32 (5H, bm), 3.20 (1H, bm), 3.11 (2H, bm), 3.03 (2H, bm), 2.36 (2H, t; J=7.4 Hz), 1.81 (1H, bm), 1.70-1.20 (5H), 1.24 (3H, d; J=6.5 Hz) ppm.

$^{13}$C NMR (d$_6$-DMSO): 171.11, 150.40, 139.39, 130.76, 128.63, 127.50, 123.57, 122.93, 119.03, 111.84, 111.57, 108.51, 102.08, 53.05, 44.15, 36.06, 31.95, 24.77, 24.42, 22.02, 15.56 ppm.

Example 4

5-[[2-(5-Hydroxy-1H-indol-3-yl)ethyl]amino]-N-[4-(trifluoromethyl)phenyl]-hexanamide, monohydrochloride Serotonin hydrochloride hemihydrate (200 mg) and N-[4-(trifluoromethyl)phenyl]-5-oxo-hexanamide (246 mg) were stirred under nitrogen in methanol (8 mL) and treated with sodium cyanoborohydride (85 mg). After stirring 66 hours at 23° C., sodium bicarbonate (250 mg) and water (5 mL) were added. Thirty minutes later, the reaction was diluted with water (50 mL) and extracted with 1:4 2-propanol:dichloromethane (40 mL, 40 mL, 20 mL) and the extracts dried (Na$_2$SO$_4$) and concentrated in vacuo to an oil. The oil was chromatographed with 5:10:90, then 3:50:50 triethylamine:ethanol:ethyl acetate to isolate a component with R$_f$ of 0.15 (5:10:90 triethylamine:ethanol:ethyl acetate). This oil was dissolved in ethanol (50 mL), treated with 1:9 concentrated hydrochloric acid:ethanol (2 mL), and concentrated in vacuo. Reconcentration from ethanol (50 mL) and placing under vacuum gave the title compound as an off-white solid (272 mg).

IR(KBr): 3334, 1604, 1538, 1410, 1324, 1186, 1164, 1114, 1068 cm$^{-1}$.

CIMS (CH$_4$): 434 (100%) 414 (32%), 287 (34%) 142 (20%).

$^1$H NMR (d$_6$-DMSO): 10.69 (1H, d; J=2.2 Hz), 10.56 (1H, s), 8.97 (1H, bs), 8.84 (1H, bs), 8.64 (1H, s), 7.86 (2H, d; J =9.1 Hz), 7.63 (2H, d; J=9.0 Hz), 7.16 (2H, m), 6.97 (1H, d; J=2.0 Hz), 6.64 (1H, dd; J=2.1, 8.5 Hz), 3.26 (1H, m), 3.12 (2H, bm), 3.03 (2H, bm), 2.43 (2H, t; J=7.4 Hz), 1.90–1.47 (4H), 1.27 (3H, d; J=6.6 Hz) ppm.

$^{13}$C NMR (d$_6$-DMSO): 171.60, 150.40, 142.87, 130.76, 127.49, 126.22, 125.97 (m), 123.58, 123.19, 122.76, 118.87, 111.84, 111.57, 108.48, 102.08, 52.98, 44.20, 35.91, 31.77, 21.99, 20.81, 15.62 ppm.

$^{19}$F NMR (d$_6$-DMSO): −60.104 ppm.

Example 5

6-[[2-(5-Hydroxy-1H-indol-3-yl)ethyl]amino]-N-(4-methoxyphenyl)-heptanamide monohydrochloride In an aluminum foil-wrapped flask were placed N-(4-methoxyphenyl)-6-oxo-heptanamide (225 mg), 5-hydroxytryptamine hydrochloride hemihydrate (200 mg), sodium cyanoborohydride (85 mg) and methanol (8.0 mL). This mixture was stirred at room temperature (ca. 23° C.) for 67 hours. Solid sodium bicarbonate (500 mg) and water (45 mL) were added and after 5 minutes the reaction was extracted with 1:4 2-propanol:dichloromethane (3×35 mL). The combined extracts were dried with sodium sulfate, filtered, and concentrated in vacuo to a foaming oil. This was chromatographed using 5:10:90, then 3:50:50 triethylamine:ethanol:ethyl acetate isolating the component with an R$_f$ of 0.15 in 5:10:90 triethylamine:ethanol:ethyl acetate. The product was twice reconcentrated from ethanol (100 mL), then redissolved in ethanol (100 mL) and treated with 1.0M aqueous hydrochloric acid (1.5 mL). This solution was concentrated in vacuo, then twice redissolved in ethanol (70 mL) and reconcentrated. The resulting oil was placed under vacuum causing it to foam to a light tan solid (360 mg), the title compound.

Anal. Calc. C$_{24}$H$_{31}$N$_3$O$_3$.HCl.0.05 C$_2$H$_5$OH.0.8 H$_2$O:C, 62.56; H, 7.38; N, 9.08. Found: C, 62.41; H, 7.12; N, 8.94.

IR(KBr): 3404, 3270, 1652, 1512, 1244 cm$^{-1}$.

CIMS (CH$_4$): 410 (100%), 263 (32%).

$^1$H NMR (d$_6$-DMSO): 10.69 (1H, d; J=2.1 Hz), 9.91 (1H, s), 8.95 (2H, bd), 7.53 (2H, d; J=9.1 Hz), 7.15 (2H, m), 6.85 (2H, d; J=9.2 Hz), 6.86 (1H, d; J=9.3 Hz), 6.64 (1H, dd; J=2.2, 8.6 Hz), 3.70 (3H, s), 3.20 (1H, bm), 3.10 (2H, bm), 3.00 (2H, bm), 2.32 (2H, t; J=7.4 Hz), 1.81 (1H, bm), 1.59 (2H, bm), 1.33 (2H, bm), 1.24 (3H, d; J=6.5 Hz) ppm.

$^{13}$C NMR (d$_6$-DMSO): 170.55, 154.96, 150.40, 132.58, 130.76, 127.50, 123.57, 113.73, 111.84, 111.57, 108.52, 102.07, 55.13, 53.05, 44.15, 35.91, 31.94, 24.83, 24.43, 22.02, 15.56 ppm.

Example 6

6A)

6-Bromo-N-[4-(trifluoromethyl)phenyl]-hexanamide

Triethylamine (1.30 mL) and 4-aminobenzotrifluoride (1.21 g) were stirred in dichloromethane (35 mL) at 0° C. under nitrogen and treated with 6-bromohexanoyl chloride (1.15 mL). After 20 minutes, the reaction was allowed to warm to 20° C. and stirred an additional 40 minutes. The reaction was treated with aqueous saturated sodium bicarbonate (40 mL), and extracted with dichloromethane. The extracts were dried over sodium sulfate, filtered, and concentrated in vacuo to a solid. This solid was dissolved in ethyl acetate and the title compound was precipitated out as fine white needles by addition of hexanes (2.35 g). M.p. 96°-98° C.

Anal. Calc. for C$_{13}$H$_{15}$BrF$_3$NO: C, 46.17; H, 4.47; N, 4.14. Found: C, 46.25; H, 4.59; N, 4.12.

IR(KBr): 3316, 1670, 1600, 1530, 1410, 1322, 1260, 1170, 1128, 1112, 1066, 842 cm$^{-1}$.

CIMS(CH$_4$): 340 (90%), 338 (100%), 320 (50%), 318 (55%), 258 (60%).

$^1$H NMR (CDCl$_3$): 7.65 (2H, d; J=8.5 Hz), 7.56 (2H, d; J=8.5 Hz), 7.47 (1H, bs), 3.42 (2H, t; J=6.5 Hz), 2.40 (1H, t; J=6.6 Hz), 1.90 (2H, m), 1.75 (2H, m), 1.52 (2H, m) ppm.

$^{13}$C NMR (CDCl$_3$): 171.21, 140.83, 126.27, 119.32, 37.39, 33.49, 32.34, 27.64, 24.42 ppm.

$^{19}$F NMR (CDCl$_3$): −62.712 ppm.

6B) 6-Oxo-N-[4-(trifluoromethyl)phenyl]-hexanamide

A solution of sodium bicarbonate (0.250 g), potassium iodide (0.050 g), and 6-bromo-N-[4-(trifluoromethyl)phenyl]hexanamide (1.00 g) in dimethylsulfoxide (15 mL) was heated at 125°-130° C. for 3.5 hours while stirring under a nitrogen atmosphere. The reaction was treated with water (75 mL) and extracted with ether. The ether extract was washed with brine (50 mL), dried over sodium sulfate after adding dichloromethane (30 mL), filtered, and concentrated in vacuo. Chromatography using 50/50 ethyl acetate/hexane gave a white solid (R$_f$=0.2 in same solvent system, 0.326 g), identified as the title compound. m.p.: 129.5°-131.0° C.

Calc. Anal. for C$_{13}$H$_{14}$F$_3$NO$_2$: C, 57.14; H, 5.16; N, 5.13. Found: C, 57.00; H, 5.14; N, 5.01.

IR(KBr): 33.68, 2944, 2844, 1716, 1702, 1614, 1602, 1542, 1466, 1408, 1388, 1372, 1320 1308, 1258, 1168, 1110, 1064, 862, 736 cm$^{-1}$.

CIMS (CH$_4$): 274 (100%) 254 (74%).

$^1$H NMR (CDCl$_3$): 9.83 (1H, s), 7.69 (2H, d; J=9.5 Hz), 7.57 (2H, d; J=8.5 Hz), 7.63 (1H, bs), 2.56 (2H, t; J=7.6 Hz), 2.44 (2H, t; J=7.6 Hz), 1.83–1.65 (4H, m) ppm.

$^{19}$F NMR(CDCl$_3$): −60.169 ppm.

6C)

6-[[2-(5-Hydroxy-1H-indol-3-yl)ethyl]amino]-N-[4-(trifluoromethyl)phenyl]-hexanamide, monohydrochloride, hemihydrate Serotonin hydrochloride hemihydrate (120 mg) and N-[4-(trifluoromethyl)phenyl]-6-oxo-hexanamide (148 mg) were dissolved in methanol (5 mL) and treated with sodium cyanoborohydride (51 mg). The solution was stirred at ca 23° C. for 7 d in the dark. The reaction was treated with sodium bicarbonate (415 mg) and one hour later was diluted with water (50 mL) and extracted with 1:4 2-propanol:dichloromethane (3×30 mL). After drying (Na$_2$SO$_4$), the extracts were concentrated in vacuo to a clear, slightly brown oil. This oil was chromatographed using 5:10:90, then 5:50:50 triethylamine:ethanol:ethyl acetate. The component with an R$_f$ of 0.3 in the latter solvent system was isolated as an oil (140 mg), then dissolved in ethanol (20 mL) and treated with 1M hydrochloric acid (0.4 mL). The resulting solution was concentrated in vacuo, reconcentrated from ethanol (20 mL), then reconcentrated from a methanol (20 mL) and water (5 mL) mixture to give, after placing under vacuum, the title compound as a tan powder (131 mg).

Anal. calc. for $C_{23}H_{26}N_3O_2F_3 \cdot HCl \cdot 0.5\ H_2O$: C, 57.68; N, 5.89; H, 8.77. Found: C, 57.44; H, 5.89; N, 8.64.

IR(KBr) 3346, 3264, 1602, 1532, 1460, 1410, 1324, 1184, 1164, 1116, 1066 cm$^{-1}$.

CIMS (CH$_4$): 434 (100%), 414 (34%), 287 (25%).

$^1$H NMR (CD$_3$OD): 7.77 (2H, d; J=9.1 Hz), 7.58 (2H, d; J=9.0 Hz), 7.18 (1H, d; J=9.0 Hz), 7.12 (1H, s), 6.95 (1H, d; J=2.1 Hz), 6.69 (1H, dd; J=2.0, 9.1 Hz), 3.35–3.25 (2H, m), 3.09–3.00 (4H, m), 2.44 (2H, t; J=7.5 Hz), 1.69–1.55 (4H), 1.50–1.38 (2H) ppm.

$^{13}$C NMR (CD$_3$OD): 174.50, 151.57, 133.22, 128.85, 127.09, 127.04, 126.99, 126.94, 124.98, 120.66, 113.05, 112.87, 109.28, 103.13, 49.18, 47.71, 37.44, 27.08, 26.95, 25.89, 23.48 ppm.

$^{19}$F NMR (CD$_3$OD): −63.309 ppm.

Example 7

7A)

6-Oxo-N-(3,4-dimethoxyphenyl)-6-oxo-heptanamide

Prepared as in *J. Med. Chem.* 26, 492–499 (1983), Method C, except substituting 4-amino-veratrole for p-(n-butyl) aniline. N-Ethylmorpholine was used instead of N-methylmorpholine. Title compound was purified by recrystallization from hot ethyl acetate by the addition of 30:70 ethyl acetate:hexane. The title compound was obtained as a greyish-white solid.

Anal. Calc. for $C_{15}H_{21}NO_4$: C, 64.50; H, 7.58; N, 5.01. Found: C, 64.40; H, 7.66; N, 5.00.

CIMS (CH$_4$): 280 (100%), 127 (8%)

IR(KBr): 3364, 2938, 2906, 1708, 1690, 1606, 1546, 1516, 466, 1442, 1312, 1400, 1374, 1258, 1234, 1214, 1158, 1134, 1028, 764 cm$^{-1}$.

$^1$H NMR (CDCl$_3$): 7.53 (1H, bs), 7.41 (1H, d; J=2.5 Hz), 6.91 (1H, dd; J=2.5, 8.6 Hz), 6.80 (1H, d; J=8.6 Hz), 3.88 (3H, s), 3.86 (3H, s), 2.51 (2H, bt; J=6.7 Hz), 2.36 (2H, bt; J=6.8 Hz), 2.16 (3H, s), 1.71–1.66 (4H, bm) ppm.

$^{13}$C NMR (CDCl$_3$): 209.06, 170.71, 148.98, 145.69, 131.69, 111.64, 111.27, 104.86, 56.09, 55.86, 43.21, 37.22, 29.99, 24.83, 22.98 ppm.

Melting Point: 114°–115° C.

7B)

6-[[2-(5-Hydroxy-1H-indol-3-yl)ethyl]amino]-N-(3,4-dimethoxyphenyl)-heptanamide, monohydrochloride hydrate The compound was prepared as in Example 2B except using 178 mg of serotonin hydrochloride and using N-(3,4-dimethoxyphenyl)-6-oxo-heptanamide (225 mg), running the reaction 21 hours at ca. 25° C. The compound as the free amine had an R$_f$ of 0.5 in 10:90 ethanol:ethyl acetate. The title compound was obtained as a tan solid (247 mg).

Anal. Calc. for $C_{25}H_{33}N_3O_4 \cdot HCl \cdot 0.3\ H_2O$: C, 62.37; H, 7.24; N, 8.73. Found: C, 62.58; H, 7.41; N, 8.74.

IR(KBr): 3348, 1610, 1514, 1450, 1224, 1020, 792 cm$^{-1}$.

CIMS (CH$_4$):440 (100%), 293 (37%).

$^1$H NMR (d$_6$-DMSO): 10.67 (1H, d; J=2.2 Hz), 9.84 (1H, s), 8.75 (1H, bs), 8.70 (1H, s), 7.33 (1H, d; J=2.3 Hz), 7.17–7.09 (3H, m), 6.87–6.84 (2H, m), 6.63 (1H, dd; J=2.2 Hz, 8.5 Hz), 3.70 (6H, s), 3.22 (1 H, bm), 3.22 (2H, bm), 2.98 2H, bm), 2.31 (2H, bt; J=7.4 Hz), 1.85–1.70 (1H, bm), 1.63–1.32 (4H, bm), 1.23 (2H, d; J=6.4 Hz) ppm.

$^{13}$C NMR (d$_6$-DMSO): 172.41, 150.64, 149.10, 145.62, 132.90, 131.52, 128.10, 124.49, 112.88, 112.62, 112.32, 109.01, 105.25, 102.77, 56.43, 56.13, 54.04, 44.88, 36.66, 32.68, 25.53, 24.96, 22.63, 16.26 ppm.

Melting Point: 214°–215° C.

Example 8

8A)

6-Oxo-6-(N,O-dimethylhydroxylamino)-N-(4-methoxyphenyl)hexanamide

6-Oxo-6-(4-methoxyphenylamino)hexanoic acid (509 mg), tetrahydrofuran (12 mL) and dimethylformamide (0.1 mL) were cooled to 0°–5° C. Oxalyl chloride (0.23 mL) was added and the reaction was allowed to stir for fifteen minutes before the addition of N,O-dimethylhydroxylamine hydrochloride (221 mg). After twenty minutes, pyridine (0.8 mL) was added and reaction was warmed to 20°–25° C. Saturated sodium bicarbonate solution (100 mL) was added and the reaction was extracted with dichloromethane (2×30 mL). The combined organic extracts were dried (Na$_2$SO$_4$) and concentrated in vacuo to afford a brown oil which was purified by chromatography eluting with 95:5 ethyl acetate:hexanes. The resulting white solid was recrystallized from ethyl acetate:hexanes to give the title compound as white crystals (133 mg).

Anal. Calc. for $C_{15}H_{22}N_2O_4$: C, 61.21; H 7.53; N, 9.52. Found: C, 61.45; H, 7.64; N, 9.35.

CIMS (CH$_4$): 295 (85%), 234 (100%), 172 (70%).

IR(KBr): 3354, 2952, 1688, 1659, 1602, 1546, 1510, 1472, 1238, 1174, 1032, 844, 526 cm$^{-1}$.

$^1$H NMR (d$_6$-DMSO): 8.58 (1H, bs), 7.48 (2H, d; J=9.0 Hz), 6.82 (2H, d; J=9.0 Hz), 3.76 (3H, s), 3.66 (3H, s), 3.17 (3H, s), 2.47 (2H, bm), 2.38–2.34 (2H, bm), 1.76–1.69 (4 H, bm) ppm.

$^{13}$C NMR (d$_6$-DMSO): 170.82, 131.36, 121.66, 114.05, 77.21, 77.15, 76.80, 61.22, 55.47, 37.17, 31.33, 25.22, 23.60 ppm.

Melting point: 89°–90° C.

8B) N-(4-Methoxyphenyl)-6-oxo-7-phenylheptanamide

6-Oxo-6-(N,O-dimethylhydroxylamino)-N-(4-methoxyphenyl) hexanamide (454 mg) was dissolved in tetrahydrofuran (13 mL) and cooled to −78° C. Benzylmagnesium chloride in tetrahydrofuran (2.0M, 1.6 mL) was added and reaction was warmed to 20° C. After 24 hours, additional benzylmagnesium chloride in tetrahydrofuran (2.0M, 0.4 mL) was added. After 24 hours, 1.0M aqueous hydrochloric acid (10 mL) was added and reaction extracted using dichloromethane (2×15 mL). The combined organic extracts were dried (Na$_2$SO$_4$) and concentrated in vacuo. The resulting solid was chromatographed eluting with 30:70 ethyl acetate:hexanes to afford the title compound (R$_f$ of 0.68 in 70:30 ethyl acetate:hexanes) as white crystals (200 mg).

Anal. Calc. for $C_{20}H_{23}NO_3$: C, 73.82; H, 7.12; N, 4.30. Found: C, 73.80; H, 7.21; N, 4.25.

CIMS (CH$_4$): 326 (100%), 203 (8%).

IR(KBr): 3304, 2944, 1703, 1654, 1604, 1549, 1513, 1499, 1465, 1422, 1248, 1028, 832, 708 cm$^{-1}$.

$^1$H NMR (d$_6$-DMSO): 7.62 (1H, bs), 7.43 (1H, d; J=2.2 Hz), 7.40 (1H, d; J=2.2 Hz), 7.35–7.18 (5H, m), 6.84 (1H, d; J=2.3 Hz), 6.82 (1H, d; J=2.2 Hz), 3.77 (3H, s), 3.68 (2H, s), 2.50 (2H, bt; J=6.5 Hz), 2.27 (2H, bt; J=7.1 Hz), 1.62–1.60 (4H, m) ppm.

$^{13}$C NMR (d$_6$-DMSO): 209.19, 171.10, 156.58, 134.42, 131.29, 129.62, 129.01, 127.31, 121.90, 114.25, 55.34, 50.10, 41.23, 36.91, 24.56, 22.62 ppm.

Melting point: 131°–132° C.

8C)
ε-[[2-(5-Hydroxy-1H-indol-3-yl)ethyl]amino]-N-(4-methoxyphenyl)-benzeneheptanamide, monohydrochloride The compound was prepared as in Example 2B except using N-(4-methoxyphenyl)-6-oxo-7-phenyl-heptanamide (311 mg) and reacting components for 60 hours at 40°–45° C. Compound as the free amine had an R$_f$ of 0.74 in 1:1:8 diethylamine:ethanol:ethyl acetate. The title compound was obtained as a tan solid (90 mg).

IR(KBr): 3410, 3270, 1652, 1512, 1242, 1180, 702 cm$^{-1}$.

CIMS (CH$_4$): 486 (100%), 394 (15%), 339 (20%).

$^1$H NMR (d$_6$-DMSO): 10.68 (1H, s), 9.83 (1H, s), 9.15–9.12 (1H, bs), 8.94–8.91 (1H, bs), 8.72–8.71 (1H bs) 7.51 (2H d; J=9.1 Hz), 7.48–7.22 (5H, m), 7.17–7.11 (2H, m), 6.88–6.83 (3H, m), 6.64 (1H, dd; J=2.0, 8.5 Hz), 3.71 (3H, s), 3.22–3.12 (3H, bm), 3.08–3.01 (2H, bm), 2.83 (1H, dd; J=9.1, 13.0 Hz), 2.51 (2H, t; J=1.8 Hz), 2.23 (2H, t; J=6.9 Hz), 1.60–1.24 (6H, m) ppm.

$^{13}$C NMR (d$_6$-DMSO): 213.26, 172.32, 156.16 150.69, 146.97, 137.02, 132.43, 131.57, 129.91, 129.83, 129.58, 128.08, 127.88, 124.57, 122.04, 114.68, 112.94, 112.39, 108.94, 102.86, 59.07, 56.01, 45.45, 36.72, 36.38, 29.97, 25.63, 24.24, 22.65 ppm.

Exact Mass (CIMS, CH$_4$): Calc. for C$_{30}$H$_{36}$N$_3$O$_3$: 486.2757. Found: 486.2754.

Melting point: 109°–110° C. (started to decompose at 100° C.)

Example 9
6-[[2-(5-Hydroxy-1H-indol-3-yl)ethyl]amino]-N-(4-methoxyphenyl)octanamide, monohydrochloride The compound was prepared as in Example 2B except using N-(4-methoxyphenyl)-6-oxo-octanamide (300 mg) and running the reaction 60 hours at 35°–40° C. The compound as the free amine had an R$_f$ of 0.43 in 10:90 ethanol:ethyl acetate. The title compound was Obtained as a tan solid (238 mg).

IR(KBr): 3264, 1654, 1540, 1512, 1460, 1242 cm$^{-1}$.
CIMS (CH$_4$): 424 (100%), 277 (35%).

$^1$H NMR (d$_6$-DMSO): 10.68 (1H, d; J=1.6 Hz), 9.84 (1H, s) 8.68 (2H, bs), 7.51 (2H, d; J=8.9 Hz), 7.17–7.14 (2H, m), 6.86 (1H, s), 6.85 (2H, d; J=8.8 Hz), 6.63 (1H, dd; J=2.2 8.8 Hz), 3.7 (2H, s), 3.33–3.1 (3H, bm), 3.08–3.00 (2H, bm), 2.31 (2H, t; J=7.2 Hz), 1.68–1.598 (5H, bm), 1.38–1.15 (2H, bm), 1.06 (1H, t; J=6.9 Hz), 0.91 (3H, t; J=7.4 Hz) ppm.

$^{13}$C NMR (d$_6$-DMSO): 171.86, 155.85, 150.61, 132.45, 131.29, 127.96, 124.24, 121.62, 114.44, 112.63, 112.13, 108.87, 102.59, 58.57, 45.03, 41.99, 36.34, 28.91, 25.49, 24.34, 22.58, 22.39, 11.45 ppm.

Exact Mass (CIMS, CH$_4$) Calc. for C$_{25}$H$_{34}$N$_3$O$_3$: 424.2600. Found: 424.2621.

Example 10
5-[(2,3-Dihydro-1,4-benzodioxin-2-yl)methylamino]-N-[4(trifluoromethyl)phenyl]-pentanamide, monohydrochloride 2,3-Dihydro-1,4-benzodioxin-2-methanamine (350 mg) and 5-chloro-N-[4-(trifluoromethyl)phenyl]-pentanamide (593 mg) were stirred in dimethylformamide (7.0 mL) under a nitrogen atmosphere. Sodium bicarbonate (395 mg) and potassium iodide (40 mg) were added and mixture was stirred for 60 hours at 70°–75° C. Saturated sodium bicarbonate solution (50 mL) was added to the cooled reaction and the mixture extracted with diethyl ether (3×30 mL). The combined extracts were dried (MgSO$_4$), filtered, and concentrated in vacuo. The resulting oil was chromatographed eluting with 40:60 ethyl acetate:hexane, then 10:90 ethanol:ethyl acetate to give a yellow-white solid with an R$_f$ of 0.15 in 50:50 ethyl acetate:ethanol. This solid was dissolved in ethanol (20 mL) and treated with 1.0M aqueous HCl (1.0 mL). The solution was concentrated in vacuo to a white solid which after recrystallization from ethanol:ethyl acetate afforded the title compound as a white powder (117 mg).

Anal. Calc. for C$_{21}$H$_{23}$F$_3$N$_2$O$_3$.HCl: C, 56.70; H, 5.44; N, 6.30. Found: C, 56.57; H, 5.62; N, 6.03.

CIMS (CH$_4$): 409 (100%), 273 (20%).

IR (KBr): 3442, 3316, 2954, 2934, 2844, 1670, 1600, 1530, 1496, 1410, 1334, 1268, 1118, 1070, 836, 752 cm$^{-1}$.

$^1$H NMR (d$_6$-DMSO): 10.49 (1H, s), 9.25 (1H, bs), 7.84 (2H, d; J=8.6 Hz), 7.66 (2H, d; J=8.5 Hz), 6.94–6.85 (4H, m), 4.65–4.63 (1H, m), 4.36 (1H, dd; J=2.5, 11.6 Hz), 4.06 (1H, dd; J=6.7, 11.7 Hz), 3.30 (1H, m), 3.20 (1H, m), 3.03–2.98 (2H, bm), 2.41 (2H, bt), 1.68–1.64 (4H, bm) ppm.

$^{13}$C NMR (d$_6$-DMSO): 171.55, 142.83, 141.82, 125.95 (m), 123.19, 122.75, 121.71, 118.83, 117.35, 117.12, 69.16, 64.79, 47.14, 46.35, 35.70, 24.84, 21.94 ppm.

$^{19}$NMR (d$_6$-DMSO): −60.08 ppm (s).

Melting point: 190°–192° C.

Example 11
6-[(2,3-Dihydro-1,3-benzodioxin-2-yl)methylamino]-N-[3-(trifluoromethyl)phenyl]-hexanamide, monohydrochloride The title compound was prepared according to Example 10 except using 6-bromo-N-[3-(trifluoromethyl)-phenyl]hexanamide. The reaction required 57 hours at 40°–45° C. The title compound (R$_f$ of 0.51 in 1:1:8 diethylamine:ethanol:ethyl acetate) was obtained as a yellow solid (380 mg).

Anal. Calc. for C$_{22}$H$_{25}$F$_3$N$_2$O$_3$.HCl: C, 57.58; H, 5.71; N, 6.10. Found: C, 57.35; H, 5.94; N, 5.81.

IR (KBr): 3440, 2944, 2786, 1660, 1496, 1448, 1336, 1132, 1068, 756, 698 cm$^{-1}$.

CIMS (CH$_4$): 423 (100%), 403 (29%), 287 (29%).

$^1$H NMR (d$_6$-DMSO): 10.45 (1H, s), 9.35 (1H, bs), 9.07 (1H, bs), 8.16 (1H, s), 7.82 (1H, d; J=8.2 Hz), 7.53 (1H, bt; J=8.2 Hz), 7.38 (1H, d; J=8.0 Hz), 6.93–6.85 (4H, m), 4.69–4.62 (1H, bm), 4.38 (1H, dd; J=2.4, 11.7 Hz), 4.06 (1H, dd; J=6.7, 11.7 Hz), 3.30 (1H, bs), 3.19 (1H, bs), 3.01–2.94 (2H, bm), 2.38 (2H, t; J=7.1 Hz), 1.75–1.58 (4 H), 1.42–1.34 (2H) ppm.

$^{13}$C NMR (d$_6$-DMSO): 171.70, 142.68, 141.83, 140.08, 129.85, 129.33 (q), 125.95, 122.46, 122.32, 121.69, 119.24, 117.34, 117.11, 115.00 (m), 69.14, 64.80, 47.19, 46.27, 36.02, 25.53, 25.01, 24.38 ppm.

$^{19}$F NMR (d$_6$-DMSO): −61.16 ppm (s).

Melting point: Compound became gummy at 105° C., melted at 113°–114° C.

Example 12

6-[(2,3-Dihydro-1,4-benzodioxin-2-yl)methylamino]-N-[4-(trifluoromethyl)phenyl]-hexanamide, monohydrochloride 2,3-Dihydro-1,4-benzodioxin-2-methanamine (380 mg) and 6-bromo-N-[4-(trifluoromethyl)phenyl]-hexanamide (772 mg) were stirred in 1-methyl-2-pyrrolidinone (7.8 mL) under a nitrogen atmosphere. Triethylamine (0.6 mL) was added and mixture was stirred for 36 hours at 20° C., then heated at 40°-50° C. for six hours. Saturated sodium bicarbonate solution (20 mL) was added to the cooled reaction and the mixture extracted with diethyl ether (2×20 mL). The combined extracts were dried (MgSO$_4$), filtered, and concentrated in vacuo. The resulting clear liquid was chromatographed eluting with 50:50 ethyl acetate:hexane, then 5% ammonium hydroxide:ethyl acetate to give a clear oil with an R$_f$ of 0.71 in the latter solvent system. This oil was dissolved in ethanol (50 mL) and treated with 1.0M aqueous hydrochloric acid (3.0 mL). The solution was concentrated in vacuo to a yellow solid which was triturated with ethyl acetate to give the title compound as a tan solid (400 mg).

Anal. Calc. for $C_{22}H_{25}F_3N_2O_3 \cdot HCl$: C, 57.58; H, 5.71; N, 6.10. Found: C, 57.54; H, 5.81; N, 6.02.

IR (KBr): 3436, 2940, 1672, 1604, 1530, 1494, 1410, 1326, 1266, 1114, 1068, 750 cm$^{-1}$.

$^1$H NMR (d$_6$-DMSO): 10.47 (1H, s), 9.17 (2H, bs), 7.85 (2H, d; J=8.5 Hz), 7.66 (2H, d; J=8.7 Hz), 6.95–6.86 (4H, m), 4.68–4.63 (1H, bm), 4.38 (1H, dd; J=2.3, 11.6 Hz), 4.06 (1H, dd; J=6.7, 11.7 Hz), 3.27 (1H, m), 3.20 (1H, m), 2.98 (2H, m), 2.40 (2H, t; J=7.4 Hz), 1.73–1.61 (4H, m), 1.42–1.35 (2H, m) ppm.

CIMS (CH$_4$): 423 (100%), 403 (30%).

$^{19}$F NMR (d$_6$-DMSO): −60.112 ppm(s).

Melting point: 191.0°–191.5° C.

Example 13

6-[[(2,3-Dihydro-1,4-benzodioxin-2-yl)methyl]methylamino]-N-[4-(trifluoromethyl)phenyl]-hexanamide monohydrochloride 6-[(2,3-Dihydro-1,4-benzodioxin-2-yl)methylamino]-N-[4-(trifluoromethyl)phenyl]hexanamide monohydrochloride (201 mg), 37% aqueous formaldehyde (0.18 mL) and sodium cyanoborohydride (38 mg) were stirred in methanol (4.8 mL) for 96 hours at 20°-25° C. under nitrogen atmosphere. Saturated sodium bicarbonate (20 mL) was added to the reaction and extracted with dichloromethane (2×20 mL). The combined extracts were dried (Na$_2$SO$_4$) and concentrated in vacuo. The resulting oil was chromatographed eluting with ethyl acetate and 10:90 ethanol:ethyl acetate to give a white solid (R$_f$ of 0.52 in 10:90 ethanol:ethyl acetate) which was dissolved in ethanol and treated with 1.0M aqueous HCl (1 ml). The solution was concentrated in vacuo to give an oil which was dissolved in 70:30 ethyl acetate:hexane and concentrated. A hygroscopic white solid (151 mg) remained.

CIMS (CH$_4$): 437 (100%), 301 (40%).

Exact Mass (CIMS, CH$_4$): Calc. for $C_{23}H_{23}F_3N_2O_3$: 437.2052. Found: 437.2044.

IR (KBr): 3432, 1688, 1604, 1538, 1496, 1410, 1324, 1264, 1114, 1066, 846, 752 cm$^{-1}$.

$^1$H NMR (d$_6$-DMSO): 10.82 (1H, bs), 10.59 (1H, bs), 10.48 (1H, s), 7.85 (2H, d; J=8.6 Hz), 7.66 (2H, d; J=8.8 Hz), 6.95–6.86 (4H, m), 4.86 (1H, bs), 4.35 (1H, d; J=10.7 Hz), 4.09–4.00 (1H, m), 3.60–3.10 (multiple broad multiplets), 2.91–2.79 (3H, bs), 2.51 (2H, s), 2.41 (2H, t; J=6.9 Hz), 1.74–1.58 (4H, bm), 1.40–1.29 (2H, bm) ppm.

$^{19}$F NMR (d$_6$-DMSO): −60.075 ppm(s).

Example 14

4-[[2-(5-Hydroxy-1H-indol-3-yl)ethyl]amino]-N-[4-(trifluoromethyl)phenyl]-pentanamide, hydrochloride, monohydrate Prepared as in Example 1 except substituting 4-oxo-N-[4-(trifluoromethyl)phenyl]-pentanamide for the keto amide. The title compound was isolated as a tan solid.

Anal. Calc. for $C_{22}H_{24}F_3N_3O_2 \cdot HCl \cdot H_2O$: C, 55.76; H, 5.74; N, 8.87. Found: C, 55.74; H, 6.59; N, 8.67.

IR(KBr): 3408, 1670, 1606, 1542, 1412, 1326, 1114, 1068 cm$^{-1}$.

CIMS (CH$_4$): 420 (100%), 400 (20%), 273 (32%), 142 (92%).

$^1$H NMR (d$_6$-DMSO): 10.68 (1H, bs), 10.63 (1H, s), 9.06 (1H, bs), 8.95 (1H, bs), 8.69 (1H, bs), 7.86 (2H, d; J=8.5 Hz), 7.68 (2H, d; J=8.5 Hz), 7.17–7.11 (2H), 6.90 (1H, d; J=1.0 Hz), 6.63 (1H, dd; J=1.1, 8.3 Hz), 3.40 (4H, bs), 3.31 (1H, bs), 3.13 (2H, bm), 3.04 (2H, bm), 2.62–2.44 (2H), 2.16 (1H, bm), 1.80 (1H, m), 1.28 (3H, d; J=6.7 Hz) ppm.

$^{13}$C NMR (d$_6$-DMSO): 171.36, 150.72, 143.08, 131.08, 127.82, 126.33 123.93, 123.61, 119.24, 112.15, 111.89, 107.76, 102.39, 53.15, 44.65, 32.56, 28.22, 22.33, 15.93 ppm.

$^{19}$F NMR (d$_6$-DMSO): −60.125 ppm.

Example 15

6-[[2-(5-Methoxy-1H-indol-3-yl)ethyl]amino]-N-[4-(trifluoromethyl)phenyl]-heptanamide, hydrochloride.¾ hydrate Prepared as in Example 1 except substituting 2-(5-methoxy-1H-indol-3-yl)ethylamine hydrochloride for serotonin hydrochloride and substituting 3:35:65 triethylamine:ethanol:ethyl acetate for the second chromatography solvent. The title compound was isolated as a tan solid.

Anal. Calc. for $C_{25}H_{30}F_3N_3O_2 \cdot HCl \cdot \tfrac{3}{4} H_2O$: C, 58.70; H, 6.40; N, 8.21. Found: C, 58.82; H, 6.23; N, 8.40.

IR(KBr): 3417, 2946, 1671, 1605, 1537, 1487, 1410, 1325, 1165, 1114, 1067, 844 cm$^{-1}$.

CIMS (CH$_4$): 462 (100%), 442 (44%).

$^1$H NMR (d$_6$-DMSO): 10.82 (1H, bs), 10.48 (1H, bs), 8.88 (2H, bs), 7.84 (2H, d; J=8.0 Hz), 7.645 (2H, d; J=8.1 Hz), 7.25 (1H, d; J=8.2 Hz), 7.22 (1H, d; J=1.2 Hz), 7.11 (1H, d; J=1.0 Hz), 6.75 (1H, dd; J=1.2, 8.2 Hz), 3.77 (3H, s), 3.27–3.02 (5H), 2.41 (2H, bt), 1.82 (1H, bm), 1.60–1.20 (5H), 1.24 (3H, d; J=6.7 Hz) ppm.

$^{19}$F NMR (d$_6$-DMSO): −60.094 ppm.

Example 16

16A) 5-Oxo-N-(2-methoxyphenyl)-hexanamide

Prepared as in J. Med. Chem. 26. 492–499 (1983), Method C, except substituting orthoanisidine for p-(n-butyl)aniline. Title compound was purified by chromatography using 50:50 ethyl acetate:hexanes and then recrystallizing from hot ethyl acetate by the addition of 20:80 ethyl acetate:hexanes. The title compound was isolated as white needles. Melting point: 101.0°–101.5° C.

Anal. Calc. for $C_{14}H_{19}NO_3$: C, 67.45; H, 7.68; N, 5.62. Found: C, 67.21; H, 7.69; N, 5.45.

16B)
6-[[2-(5-Hydroxy-1H-indol-3-yl)ethyl]amino]-N-(2-methoxyphenyl)-heptanamide. hydrochloride.monohydrate Prepared as in Example 1 except substituting 6-oxo-N-(2-methoxyphenyl)-heptanamide for the keto amide and using dichloromethane to extract the crude product. The crude product was purified by chromatography using 4:10:90, then 3:30:70 triethylamine:ethanol:ethyl acetate to elute. The title compound was isolated as a tan solid.

Anal. Calc. for $C_{24}H_{31}N_3O_3.HCl.H_2O$: C, 62.13; H, 7.39; N, 9.06. Found: C, 61.91; H, 7.33; N, 8.96.

IR(KBr) 3406, 3284, 2944, 1658, 1598, 1528, 1488, 1460, 1434, 1254, 1218, 754 cm$^{-1}$.

CIMS (CH$_4$); 410 (100%,), 263 (26%).

$^1$H NMR (d$_6$-DMSO): 10.68 (1H, bs), 9.08 (1H, s), 8.94 (2H, bm), 7.92 (H, d; J=7.5 Hz), 7.15 (2H, m), 7.09-7.00 (2H), 6.90-6.85 (2H, m), 6.64 (1H, dd; J=1.3, 7.5 Hz), 3.82 (3H, s), 3.60 (2H, bm), 3.20 (1H, bm), 3.11 (2H, bm), 3.00 (2H, bm), 2.38 (2H, bt; J=7.2 Hz), 1.80 (1H, bm), 1.67-1.25 (3H), 1.26 (3H, d; J=6.5 Hz) ppm.

$^{13}$C NMR (d$_6$-DMSO): 171.16, 150.37, 149.63, 130.74, 127.47, 127.31, 124.23, 123.51, 122.11, 120.12, 111.79, 111.55, 111.07, 108.51, 102.06, 55.59, 53.03, 44.10, 35.77, 31.91, 24.88, 24.42, 21.98, 15.54 ppm.

Example 17

17A)
6-Bromo-N-[2-(trifluoromethyl)phenyl]-hexanamide

Prepared according to procedure of example 6A except using 2-aminobenzotrifluoride. The reaction took 24 hours at 20°-25° C. The title compound (R$_f$ of 0.40 in 30:70 ethyl acetate:hexane) was obtained as white crystals (2.40 g).

Anal. Calc. for $C_{13}H_{15}BrF_3NO$: C, 46.17; H, 4.47; N, 4.14. Found: C, 46.31; H, 4.53; N, 4.12.

IR(KBr): 3274, 1662, 1590, 1524, 1456, 1320, 1280, 1258, 1176, 1120, 1060, 1038, 766 cm$^{-1}$.

CIMS (CH$_4$): 338 (30%), 320 (10%), 258 (50%), 203 (40%), 161 (100%).

$^1$H NMR (CDCl$_3$): 8.0 (1H, bd; J=8.0 Hz), 7.67 (1H, bs), 7.59 (1H, d; J=7.9 Hz), 7.51 (1H, t; J=7.9 Hz), 7.22 (1H, t; J=7.6 Hz), 3.39 (2H, t; J=6.7 Hz), 2.38 (2H, t; J=7.2 Hz), 1.91-1.81 (2H, m), 1.77-1.66 (2H, m), 1.54-1.46 (2H, m) ppm.

$^{13}$C NMR (CDCl$_3$): 170.99, 135.12, 132.86, 126.06 (m), 124.56, 124.47, 37.47, 33.42, 32.40, 27.61, 24.47 ppm.

$^{19}$F NMR (CDCl$_3$): −61.27(s) ppm.

Melting point: 50°-51° C.

17B)
6-[(2,3-Dihydro-1,4-benzodioxin-2-yl)methylamino]-N-[2-(trifluoromethyl)phenyl]-hexanamide, monohydrochloride Prepared according to procedure of Example 10 except using 6-bromo-N-[2-(trifluoromethyl)phenyl]-hexanamide. Reaction took 48 hours at 35°-40° C. The title compound (R$_f$ of 0.65 in 1:1:8 diethylamine:ethanol:ethyl acetate) was obtained as a yellow solid (158 mg).

Anal. Calc. for $C_{22}H_{25}F_3N_2O_3.HCl$: C, 57.58; H, 5.75; N, 6.10. Found: C, 57.26; H, 5.75; N, 6.47.

IR(KBr): 3432, 2942, 2778, 1670, 1592, 1526, 1496, 1454, 1320, 1268, 1170, 1126, 750 cm$^{-1}$.

CIMS (CH$_4$): 423 (100%), 287 (20%).

$^1$H NMR (d$_6$-DMSO): 9.61 (1H, s), 9.47 (1H, bs), 9.22 (1H, bs), 7.75-7.51 (2H, m), 7.47 (2H, m), 6.97-6.84 (4H, m), 4.72-4.64 (1H, m), 4.38 (1H, dd; J=2.4, 11.7 Hz), 4.07 (1H, dd; J=6.7 Hz, 11.7 Hz), 3.32 (1H, m), 3.23-3.16 (1H, m), 3.04-2.91 (2H, m), 2.36 (2H, m), 1.71-1.45 (4H), 1.38-1.31 (2H, m) ppm.

$^{13}$C NMR (d$_6$-DMSO): 172.45, 143.08, 142.22, 135.94, 135.91, 133.27, 130.81, 127.02, 126.60 (m), 126.47, 125.73, 122.03, 117.64, 117.43, 69.29, 64.90, 47.26, 46.29, 35.17, 25.47, 24.99, 24.57 ppm.

$^{19}$F NMR (d$_6$-DMSO): −59.10(s) ppm.

Melting point: Title compound melted at 174°-175° C.

Example 18
6-[[2-(1-H-Indol-3-yl)ethyl]amino]-N-[4-(trifluoromethyl)-phenyl]-hexanamide, monohydrochloride Tryptamine-HCl (648 mg), 6-bromo-N-[4-(trifluoromethyl)phenyl]-hexanamide (543 mg) (prepared in Example 6A) and triethylamine (0.7 mL) were stirred in dimethylformamide (16 mL) for 60 hours at 55°-60° C. under a nitrogen atmosphere. Saturated sodium bicarbonate solution (100 mL) was added to reaction and the mixture was extracted with diethyl ether (3×50 mL). The combined extracts were dried (MgSO$_4$), filtered and concentrated. The resulting brown liquid was chromatographed eluting with 70:30 ethyl acetate:hexane and then 1:1:8 diethylamine:ethanol:ethyl acetate (R$_f$ of 0.45 in 1:1:8 dethylamine:ethanol:ethyl acetate) to give a yellow oil which was dissolved in ethanol and treated with 1.0M aqueous HCl (4.5 mL). The solution was concentrated in vacuo to give the title compound as a tan solid (284 mg).

CIMS (CH$_4$): 418 (100%) 287 (25%).

Exact Mass (CIMS, CH$_4$): Calc. for $C_{23}H_{27}F_3N_3O$: 418.2106. Found: 418.2102.

IR(KBr): 3418, 3314, 2948, 2788, 1666, 1604, 1538, 1458, 1410, 1342, 1326, 1114, 1068, 740, 580 cm$^{-1}$.

$^1$H NMR (d$_6$-DMSO): 10.99 (1H, s), 10.50 (1H, s), 9.01 (2H, bs), 7.85 (2H, d; J=8.5 Hz), 7.65 (2H, d; J=8.6 Hz), 7.60 (1H, d; J=7.8 Hz), 7.37 (1H, d; J=8.1 Hz), 7.24 (1H, d; J=2.1 Hz), 7.09 (1H, app.t.; J=7.0 Hz), 7.00 (1H, app.t.; J=6.9 Hz), 3.40 (1H, bs), 3.11 (4H, bm), 2.96-2.91 (2H, bm), 2.40 (2H, t; J=7.2 Hz), 1.71-1.60 (4H, bm), 1.39-1.34 (2H, bm) ppm.

$^{13}$C NMR (d$_6$-DMSO): 173.62, 147.03, 142.91, 136.92, 127.42, 126.92 (m), 124.02, 122.42, 120.17, 119.74, 118.97, 112.49, 109.92, 48.00 47.51, 36.85, 26.21 26.03, 25.21, 22.47 ppm.

$^{19}$F NMR (d$_6$-DMSO): −60.06 ppm(s).

Melting point: 180°-181° C.

Example 19

19A)
5-Iodo-N-[4-(trifluoromethyl)phenyl]-pentanamide

5-Chloro-N-[4-(trifluoromethyl)phenyl]-pentanamide (2.795 g) and sodium iodide (3.32 g) were stirred in acetone (20 ml) at 22° C. for 3d, then heated at reflux for 16h, all under nitrogen. The cooled reaction mixture was chromatographed with 50:50 ethyl acetate:hexane to isolate product with R$_f$=0.30 in 35:65 ethyl acetate:hexane by addition of hexane and evaporation of solvent under a stream of nitrogen afforded, after suction filtration, a white solid (2.887 g).

The product iodide contained ca. 5% starting chloride and was used without further purification.

19B)
5-[2,3-Dihydro-1,4-benzodioxin-2(R)-yl)methylamino]-N-[4-(trifluoromethyl)phenyl]-pentanamide, monohydrochloride 2,3-Dihydro-1,4-benzodioxin-2(R)-methanamine (455 mg) and 5-iodo-N-[4-(trifluoromethyl)phenyl]-pentanamide (1220 mg) were dissolved in dry dimethylformamide (24 mL) under nitrogen and heated at 65°–70° C. for 9h. The reaction was cooled, treated with saturated aqueous sodium bicarbonate (10 mL) and water (100 mL) and the resulting mixture extracted with ether (2×100 mL). The ether extracts were washed with brine, dried over $MgSO_4/Na_2SO_4$, and concentrated in vacuo to an oil. Chromatography with 0:20:80, then 5:20:80 triethylamine:ethanol:ethyl acetate gave a solid ($R_f$ ca. 0.45 in the latter system, 570 mg). This was dissolved in ethanol (15 mL), treated with 1.0M aqueous hydrochloric acid (2 mL) and concentrated in vacuo. This solid was crystallized from warm ethanol (10 mL) by addition of ether (10 mL) and cooling (0° C.). Suction filtration afforded the title compound (350 mg) as a white solid.

Anal.Calc. for $C_{21}H_{23}F_3N_2O_3 \cdot HCl$: C, 56.70; H, 5.44; N, 6.30. Found: C, 56.74; H, 5.56; N, 6.10.

IR(KBr): 2946, 2776, 1668, 1604, 1534, 1496, 1410, 1328, 1264, 1166, 1114, 1068 cm$^{-1}$.

$^1$H NMR (d$_6$-DMSO): 10.51 (1H, s), 9.20 (2H, bd), 7.84 (2H, d; J=8.6 Hz), 7.66 (2H, d; J=8.7 Hz), 6.94–6.85 (4H, m), 4.64 (1H, m), 4.37 (1H, dd; J=2.4, 11.6 Hz), 4.06 (1H, dd; J=6.7, 11.6 Hz), 3.30 (1H, m), 3.20 (1H, m), 3.01 (2H, bm), 2.41 (2H, bt), 1.66 (4H, bm) ppm.

$^{13}$C NMR (d$_6$-DMSO): 171.55, 142.85, 142.69, 141.83, 125.98, 123.18, 122.75, 121.71, 118.83, 117.35, 117.12, 69.15, 64.79, 47.11, 46.33, 35.71, 24.83, 21.95 ppm $^{19}$F NMR (d$_6$-DMSO): −60.072 ppm(s).

Melting point: 190.5°–192.0° C.

Optical rotation: $[\alpha]_D^{20}$ = +44.8° (c=1.08, methanol).

Example 20
5-[(2,3-Dihydro-1,4-benzodioxin-2(S)-yl)methylamino]-N-[4-(trifluoromethyl)phenyl]-pentanamide, monohydrochloride Prepared essentially as in Example 19B except substituting 2,3-dihydro-1,4-benzodioxin-2(S)-methanamine for the R-enantiomer.

Anal. Calc for $C_{21}H_{23}F_3N_2O_3 \cdot HCl$: C, 56.70; H, 5.44; N, 6.30. Found: C, 56.30; H, 5.62; N, 6.09.

All spectral data was essentially identical to Example 20B. Optical rotation: $[\alpha]_D^{20}$ = −44.8° (c=0.89, methanol).

Example 21
5-[(2,3-Dihydro-1,4-benzodioxin-2(S)-yl)methylamino]-N-(4-chlorophenyl)-pentanamide, monohydrochloride Prepared as in Example 19 except using 5-iodo-N-(4-chlorophenyl)-pentanamide as the alkylating agent and heating at 80° C. for 6 hours, then 70° C. for 16 hours. Crude product was chromatographed using 0:10:90, then 5:10:90 triethylamine:ethanol:ethyl acetate. Component with an $R_f$ of ca. 0.40 was isolated, converted to the hydrochloride salt, and recrystallized as in Example 19 to afford a white solid.

Anal. Calc. for $C_{20}H_{23}ClN_2O_3 \cdot HCl$: C, 58.40; H, 5.88; N, 6.81. Found: C, 58.11; H, 6.03; N, 6.71.

CIMS (CH$_4$): 377 (37%), 375 (100%), 239 (31%), 111 (30%).

IR(Kbr):2944, 2782, 1654, 1596, 1536, 1494, 1400, 1266 cm$^{-1}$.

$^1$NMR (d$_6$-DMSO): 10.26 (1H, s), 9.31 (1H, bs), 9.09 (1H, bs), 7.67 (2H, d; J=8.4 Hz), 7.34 (2H, d; J=8.3 Hz), 6.94–6.86 (4H), 4.65 (1H, m), 4.37 (1H, dd; J=2.3, 11.7 Hz), 4.06 (1H, dd; J=6.8, 11.8 Hz), 3.29 (1H, bm), 3.19 (1H, bm), 3.00 (1H, bm), 2.38 (2H, bt; J=7.0 Hz), 1.67 (4H, m) ppm.

$^{13}$C NMR (d$_6$-DMSO): 170.99, 142.67, 141.82, 138.25, 128.53, 126.47, 121.71, 120.50, 120.42, 117.35, 117.12, 69.14, 64.78, 47.13, 46.32, 35.62, 24.84, 22.02 ppm.

Melting point: 200°–202° C.

Optical rotation: $[\alpha]_D^{20}$ = −48.6° (c=0.69, methanol).

Example 22
6-[(2,3-Dihydro-1,4-benzodioxin-2-yl)methylamino]-N-(4-methoxyphenyl)-hexanamide, monohydrochloride.

Prepared as in Example 19 except using 2,3-dihydro-1,4-benzodioxin-2-methanamine (nonchiral) and using 6-iodo-N-(4-methoxyphenyl)-hexanamide as the alkylating agent. The reaction was run at 80° C. for 19 hours. The product was isolated as a white solid after chromatography, conversion to the monohydrochloride salt, and drying.

Anal. Calc. for $C_{22}H_{28}N_2O_4 \cdot HCl$. HCl: C,62.77; H, 6.94; N, 6.66. Found: C, 62.57; H, 6.96; N, 6.68.

CIMS (CH$_4$): 385 (100%), 249 (42%).

IR (KBr): 2944, 1656, 1530, 1514, 1496, 1268, 1250, 1238 cm$^{-1}$.

$^1$H NMR (d$_6$-DMSO): 9.87 (1H, S), 9.4 (1H, vbs), 9.2 (1H, vbs, 7.52 (2H, d; J=9.2 Hz), 6.95–6.85 (4H, m), 6.85 (2H, d; J=9.0 Hz), 4.66 (1H, m), 4.38 (1H, dd; J=2.4, 11.7 Hz), 4.06 (1H, dd; J=6.7, 11.6 Hz), 3.71 (3H, s), 3.19 (1H, m), 3.18 (1H, m), 2.98 (2H, m), 2.30 (2H, bt; J=7.3 Hz), 1.70 (2H, m), 1.60 (2H, m), 1.35 (2H, m) ppm.

$^{13}$C MR (d$_6$-DMSO): 170.39, 154.94, 142.68, 141.84, 132.55, 121.70, 120.53, 120.43, 117.35, 117.11, 113.71, 69.13, 64.82, 55.11, 47.16, 46.21, 35.89, 25.61, 25.00, 24.61 ppm.

Melting point: 154.5°–155.5° C.

Example 23
5-[(2,3-Dihydro-1,4-benzodioxin-2-yl)methylamino]-N-(3,4-dichlorophenyl)-pentanamide, monohydrochloride Prepared as in Example 19 except using 5-iodo-N-(3,4-dichlorophenyl)-pentanamide as the alkylating agent and using 10:90 ethanol:ethyl acetate as the eluant in the chromatography. The product was recrystallized from 50:50 methanol:ethanol by evaporation of methanol under a steam of nitrogen followed by addition of ether and isolation of the white solid.

Anal Calc. for $C_{20}H_{22}Cl_2N_2O_3 \cdot HCl$: C, 53.89,; H, 5.20; N, 6.28. Found: C, 53.76; H, 5.41; N, 6.09.

CIMS (CH$_4$); 411 (56%), 409 (100%).

IR (KBr): 2948, 1666, 1592, 1524, 1494, 1476, 1268, 750 cm$^{-1}$.

$^1$H NMR(d$_6$-DMSO): 10.44 (1H, s), 9.20 (1H, bs), 9.05 (1H, bs), 8.04 (1H, d; J=1.9 Hz), 7.58–7.50 (2H), 6.94–6.86 (4H), 4.62 (1H, m), 4.36 (1H, dd; J=2.6, 11.6 Hz), 4.06 (1H, dd; J=6.8, 11.8 Hz), 3.31 (1H, m), 3.20 (1H, m), 3.00 (2H, m), 2.39 (1H, bt; J=6.4 Hz), 1.67 (4H) ppm.

$^{13}$C NMR (d$_6$-DMSO): 171.39, 142.67, 141.79, 139.35, 130.87, 130.61, 124.34, 121.71, 120.13, 119.00, 118.92, 117.33, 117.13, 69.13, 64.74, 47.09, 46.30, 35.60, 24.77, 21.87 ppm.

Melting Point: 177°–179° C.

Example 24

6-[[2-(2,3-Dihydro-1,4-benzodioxin-2-yl)ethyl]amino]-N-phenyl-hexanamide, monohydrochloride 2-(2,3-Dihydro-1,4-benzodioxin-2-yl)ethylamine hydrochloride (1,057 mg) and 6-oxo-N-phenyl-hexanamide (403 mg) were stirred in dry methanol (25 mL) at 22° C. and treated with sodium cyanoborohydride (148 mg). After 68 hours, the reaction was treated with 1M hydrochloric acid (ca. 20 mL) and stirred 1 hour. The pH was then brought to 13 using 1.0M aqueous sodium hydroxide. Extraction with dichloromethane, drying with sodium sulfate, and concentration afforded an oil. Chromatography with 0:20:80, then 5:20:80 diethylamine:ethanol:ethyl acetate, and isolation of the component with an R$_f$ of ca. 0.25 in the latter system gave a clear oil (305 mg). This was converted to the hydrochloride salt with 1.0M hydrochloric acid and the resulting solid recrystallized from ethanol:ethyl acetate.

Anal. Calc. for C$_{22}$H$_{28}$N$_2$O$_3$.HCl: C, 65.26,; H, 7.22; N, 6.92. Found: C, 65.06; H, 7.29; N, 6.86.

CIMS (CH$_4$): 369 (100%).

IR (KBr): 3434, 2946, 1656, 1598, 1540, 1494, 1266, 754 cm$^{-1}$.

$^1$H NMR (d$_6$-DMSO): 10.00 (1H, S), 8.89 (2H, bs), 7.60 (2H, d; J=8.6 Hz), 7.28 (2H, t; J=8.7 Hz), 7.02 (1H, t; J=8.5 Hz), 6.90–6.80 (4H), 4.35–4.27 (2H), 3.92 (1H, dd; J =6.8, 11.6 Hz), 3.10 (2H, bt), 2.92 (2H, bt), 2.33 (2H, t; J=6.7 Hz), 2.00 (2H), 1.70–1.55 (4H), 1.33 (2H) ppm.

$^{13}$C NMR (d$_6$-DMSO): 171.05, 142.90, 142.56, 139.35, 128.62, 122.92, 121.42, 121.34, 119,00, 117,15, 116.92, 70.32, 66.78, 46.63, 43.04, 36.06, 26.79, 25.62, 25.29, 24.56 ppm.

Example 25

6-[[2-(5-Carboxamido-1H-indol-3-yl)ethyl]amino]-N-(4-methoxyphenyl)-heptanamide, hemifumarate.

2-(5-Carboxamido-1H-indol-3-yl)ethylamine maleate (798 mg) and 6-oxo-N-(4-methoxyphenyl)-heptanamide (623 mg) were stirred in methanol (15 mL) under nitrogen and treated with sodium cyanoborohydride (190 mg). After 20 hours at 22° C., the reaction was treated with saturated aqueous sodium bicarbonate and stirred an additional hour. The reaction was extracted with 20:80 2-propanol:dichloromethane, the extracts dried (Na$_2$SO$_4$), and concentrated to a foam. Chromatography (0:20:80, then 5:20:80 diethylamine:ethanol:ethyl acetate) gave a component with an R$_f$ of Ca. 0.45 which was converted to its hemifumarate salt, a tan solid (870 mg).

Anal. Calc. for C$_{25}$H$_{32}$N$_4$O$_3$. 0.5 C$_4$H$_4$O$_4$: C,65.57; H, 6.93; N, 11.33. Found: C, 65.27; H, 7.24; N, 11.16.

CIMS (CH$_4$). 437 (100%). 263 (45%). 117 (100%).

IR (KBr): 3382, 3190, 2946, 1656, 1602, 1568, 1512, 1366, 1234 cm$^{-1}$.

$^1$H NMR (d$_6$-DMSO): 11.15 (1H, bs), 9.80 (1H, bs), 8.27 (1H, bs), 7.96 (1H, bs), 7.66 (1H, dd; J=1.5, 8.5 Hz), 7.49 (2H, d; J=9.1 Hz), 7.35 (1H, d; J=8.5 Hz), 7.27 (1H, d; J=1.9), 7.10 (1H, bs), 6.84 (2H, d; J=9.1 Hz), 6.46 (1H, s), 3.70 (3H, s), 3.04–2.93 (5H), 2.27 (2H, bt; J=7.4 Hz), 1.69–1.52 (2H), 1.49–1.25 (2H), 1.11 (3H, d; J=6.4 Hz) ppm.

$^{13}$C NMR (d$_6$-DMSO): 170.59, 169.01, 168.63, 154.94, 137.81, 132.55, 126.48, 124.61, 124.19, 120.91, 120.56, 118.75, 113.72, 112.28, 110.73, 55.11, 52.54, 45.55, 36.06, 33.91, 25.12, 24.70, 23.57, 17.60 ppm.

Melting point: 236°–239° C.

Example 26

7-[[2-(1H-indol-3-yl)ethyl]amino]-N-phenyl-heptanamide, hemifumarate

Prepared as in Example 25 except using 2-(1H-indol-3-yl)ethylamine hydrochloride and 7-bromo-N-phenyl-heptanamide as the amine and alkylhalide. The component with an R$_f$ of ca. 0.5 in 5:20:80 diethylamine:ethanol:ethyl acetate was isolated.

Anal Calc. for C$_{23}$H$_{29}$N$_3$O.0.5 C$_4$H$_4$O: C, 71.23; H, 7.41; N, 9.97. Found: C, 70.94; H, 7.64; N, 9.70

CIMS (CH$_4$): 364 (100%), 117 (100%).

IR(KBr): 3408, 3248, 2936, 1674, 1620, 1600, 1550, 1500, 1458, 1442, 1360, 752 cm$^{-1}$.

$^1$H NMR (d$_6$-DMSO): 10.95 (1H, bs), 10.03 (1H, s), 7.61 (2H, dd; J=1.1, 8.6 Hz), 7.56 (1H, d; J=7.8 Hz), 7.35 (1H, d; J=7.9 Hz), 7.29–7.24 (2H), 7.18 (1H, d; J=2.4 Hz), 7.09–6.95 (4H), 6.45 (1H, s), 2.99 (4H, bs), 2.78 (2H, bt; J=7.3 Hz), 2.30 (2H, t; J=7.2 Hz), 1.60–1.53 (4H), 1.32–1.27 (4H) ppm.

$^{13}$C NMR (d$_6$-DMSO): 171.28, 169.33, 139.44, 136.26, 128.65, 126.97, 122.99, 122.90, 121.04, 119.03, 118.35, 118.27, 111.46, 110.64, 48.04, 47.27, 36.30, 28.32, 26.71, 26.12, 25.00, 22.96 ppm.

Melting Point: 180°–182° C.

Example 27

5-[(2,3-Dihydro-1,4-benzodioxin-2(S)-yl)methylamino]-N-(4-carboxamidophenyl)-pentanamide, hydrochloride Prepared as in Example 19 except using 5-iodo-N-(4-carboxamidophenyl)-pentanamide as the alkylating agent. The product was isolated as an off-white solid.

CIMS (CH$_4$): 384 (100%), 248 (28%).

IR(KBr): 3373, 1663, 1607, 1528, 1495, 1412, 1264, 755 cm$^{-1}$.

$^1$H NMR (d$_6$-DMSO): 10.32 (1H, s), 9.29 (1H, bs), 9.07 (1H, bs), 7.85 (1H, bs), 7.82 (2H, d; J=8.6 Hz), 7.68 (2H, d; J =8.6 Hz), 7.23 (1H, bs), 6.95–6.84 (4H), 4.64 (1H, m), 4.37 (1H, dd; J=2.4, 11.6 Hz), 4.06 (1H, dd; J=6.6, 11.4 Hz), 3.31 (1H, m), 3.20 (1H, m), 3.00 (1H, m), 2.40 (2H, bt), 1.79–1.63 (4H) ppm.

$^{13}$C NMR (d$_6$-DMSO): 171.20, 167.33, 142.66, 141.88, 128.51, 128.30, 121.70, 118.02, 117.34, 117.11, 69.14, 64.77, 47.14, 46.34, 35.68, 24.85, 21.99 ppm.

Melting Point: 154°–156° C. (dec.).

Optical rotation: [α]$_D^{20}$= −32.3° (c=0.875, dimethyl sulfoxide).

Example 28

5-[(2,3-Dihydro-1,4-benzodioxin-2-yl)methylamino]-N-(4-methylphenyl)-pentanamide, monohydrochloride.

Prepared as in Example 20 except using 5-iodo-N-(4-methylphenyl)-pentamide as the alkylating agent and heating at 70° C. for 18 hours. The crude product was chromatographed using 20:80 ethanol:ethyl acetate. The component with an R$_f$ of ca. 0.50 (in 5:20:80 triethyl amine:ethanol:ethyl acetate) was isolated, converted to the hydrochloride salt, and recrystallized as in Example 19 to afford a white solid.

Anal. calc. for C$_{21}$H$_{26}$N$_2$O$_3$.HCl: C, 64.52; H, 6.98; N, 7.16. Found: C, 64.28; H, 7.00; N, 7.15.
CIMS (CH$_4$): 355 (100%).
IR(KBr): 2944, 2716, 1661, 1596, 1524, 1496, 1265 cm$^{-1}$.
$^1$H NMR (d$_6$-DMSO): 10.01 (1H, s), 7.51 (2H, d; J=8.4 Hz), 7.08 (2H, d; J=8.3 Hz) 6.95–6.84 (4H, m), 4.68 (1H, m), 4.38 (1H, dd; J=2.4, 11.6 Hz), 4.06 (1H, dd; J=6.7, 11.7 Hz) 3.29 (1H, bm), 3.17 (1H, dd; J=8.4, 13.3 Hz) 3.00 (2H, bm), 2.51 (1H, m), 2.35 (2H, t; J=6.8 Hz) 2.24 (3H, s), 1.70 (4H, bm) ppm.
$^{13}$C NMR (d$_6$-DMSO): 170.58, 142.69, 141.86, 136.83, 131.79, 128.97, 121.70, 119.04, 117.37, 117.11, 69.15, 64.84, 47.14, 46.33, 35.63, 24.89, 22.19, 20.43 ppm.
Melting Point: 186°–187° C.

Example 29

7-[[2-(5-Hydroxy-1H-indol-3-yl)ethyl]amino]-N-phenylheptanamide, hydrochloride

Prepared as in Example 6 utilizing the appropriate reagents to obtain the title compound which was isolated as a brownish, hygroscopic solid.
CIMS (CH$_4$): 380 (100%), 233 (20%), 221 (21%).
Exact mass (CI, C$_4$H$_{10}$) calc.: 380.2338 for free amine. Found: 380.2332.
IR(KBr): 3402, 3130, 2938, 1660, 1598, 1542, 1498, 1492, 1460, 1442, 758 cm$^{-1}$.
$^1$H NMR (d$_6$-DMSO) 10.66 (1H, d; J=2.2 Hz), 9.97 (1H, s), 8.92–8.98 (2H), 7.61 (2H, d; J=7.6 Hz), 7.28 (2H, app.t; J =7.9 Hz), 7.15 (1H, d; J=8.6 Hz), 7.12 (1H), 7.01 (1H, app.t; J=7.5 Hz), 6.86 (1H, d; J=2.2 Hz), 6.63 (1H, dd; J =2.2, 8.6 Hz), 3.14–3.06 (2H), 3.00–2.87 (4H), 2.32 (2H, t; J=7.3 Hz), 1.65–1.55 (4H), 1.35–1.25 (4H) ppm.

Example 30

6-[[2-(5-Hydroxy-1H-indol-3-yl)ethyl]amino]-N-[3-(trifluoromethyl)phenyl]-hexanamide, hydrochloride The title compound was prepared as in Example 6 but using the appropriate reagents to obtain thte desired substitutions. The product was a brownish, hygroscopic solid.
Anal. Calc. for C$_{23}$H$_{26}$F$_3$N$_3$O$_2$.HCl.0.8H$_2$O: C, 57.04; H, 5.95; N, 8.68. Found: C, 57.00; H, 5.92; N, 8.69.
CIMS (CH$_4$): 434 (100%).
$^1$H NMR (d$_6$-DMSO): 10.66 (1H, m), 10.39 (1H, s), 8.74–8.66 (2H), 8.5 (1H, s), 7.78 (1H, dd; J=1.4, 7.8 Hz), 7.54 (1H, t; J=7.8 Hz), 7.38 (1H, d; J=7.8 Hz), 7.14 (1H, d; J =8.7 Hz), 7.12 (1H, d; J=2.2 Hz), 6.85 (1H, d; J=2.2 Hz), 6.63 (1H, dd; J=2.2, 8.7 Hz), 3.15–3.05 (2H), 3.00–2.90 (4H), 2.38 (2H, t; J=7.1 Hz), 1.70–1.60 (4H), 1.38–1.31 (2H) ppm.
$^{19}$F NMR (d$_6$-DMSO): −61.149 (s) ppm.

Example 31

6-[[2-(5-Hydroxy-1H-indol-3-yl)ethyl]amino]-N-[2-(trifluoromethyl)phenyl]-hexanamide, hydrochloride The title compound was prepared as in Example 6 substituting the appropriate reactants as required in Scheme I. The product is a brown, hygroscopic solid.
CIMS (CH$_4$): 434 (100%), 287 (26%). Exact mass (CIMS) calc. for C$_{23}$H$_{26}$F$_3$N$_3$O$_2$ (free amine of title: 434.2055. Found: 434.2068.
IR(KBr): 3258, 2950, 1662, 1586, 1522, 1492, 1456, 1320, 1170, 1128, 1112, 770 cm$^{-1}$.
$^1$H NMR (d$_6$-DMSO): 10.67 (1H, bs), 9.59 (1H, s), 8.82–8.72 (2H), 7.73 (1H, d; J=7.6 Hz), 7.67 (1H, t; J=7.6 Hz), 7.48–7.43 (2H), 7.15 (1H, d; J=8.7 Hz), 7.12 (1H, d; J =2.1 Hz), 6.85 (1H, d; J=2.3 Hz), 6.63 (1H, dd; J=2.4, 8.6 Hz), 3.16–3.09 (2H), 2.98–2.89 (4H), 2.35 (2H, bt), 1.67–1.55 (4H), 1.38–1.30 (2H) ppm.
$^{19}$F NMR (d$_6$-DMSO): −59.104

Example 32

5-[(2,3-Dihydro-1,4-benzodioxin-2-yl)methylamino]-N-[4-(dimethylamino)phenyl]-pentanamide, dihydrochloride The title compound was prepared as in Example 19 substituting the appropriate alkylating reactant. The product was a very hygroscopic white solid.
IR(KBr): 3434, 1550, 1516, 1494, 1266, 840 cm$^{-1}$.
CIMS (CH$_4$): 384 (100%).
$^1$H NMR (d$_6$-DMSO+D$_2$O): 7.67 (2H, d; J=9.1 Hz), 7.41 (2H, d; J=9.1 Hz), 7.00–6.91 (4H), 4.55 (1H, bm), 4.34 (1H, dd; J=2.2, 11.7 Hz), 4.02 (1H, dd; J=6.8, 11.6 Hz), 3.31 (1H, dd; J=3.1, 13.6 Hz), 3.22 (1H, dd; J=9.2, 13.6 Hz), 3.10 (6H, s), 3.04 (2H, bt), 2.39 (2H, bt), 1.68 (4H) ppm.
$^{13}$C NMR (d$_6$-DMSO+D$_2$O): 172.56, 143.24, 142.33, 138.02, 122.87, 122.76, 121.37, 120.12, 118.30, 117.94, 69.72, 65.37, 47.94, 47.13, 45.56, 36.16, 25.47, 22.60 ppm.

Example 33

7-[(2,3-Dihydro-1,4-benzodioxin-2-yl)methylamino]-N-[4-(trifluoromethyl)phenyl]-heptanamide, hydrochloride The title compound was prepared as in Example 19, except using 7-bromo-N-[4-(trifluoromethyl)phenyl]-heptanamide as the alkylating agent. The product is a white solid.
Melting point: 208°–210° C.
Anal. Calc for C$_{23}$H$_{27}$F$_3$N$_2$O$_3$.HCl: C, 58.41; H, 5.97; N, 5.92. Found: C, 58.35; H, 6.07; N, 5.76.

Example 34

5-[(2,3-Dihydro-1,4-benzodioxin-2-yl)methylamino]-N-phenylpentanamide, monohydrochloride Prepared as in Example 19 except using 5-iodo-N-phenylpentamide as the alkylating agent and heating at 82° C. for 15.5 hours. The crude product was chromatographed using 3:10:90 diethylamine:ethanol:ethyl acetate. The component with an R$_f$ of ca. 0.50 (in 5:20:80 triethyl amine:ethanol:ethyl acetate) was isolated, converted to the hydrochloride salt, and recrystallized as in Example 19 to afford a white solid.
Anal. calc. for C$_{20}$H$_{24}$N$_2$O$_3$.HCl: C, 63.73; H, 6.70; N, 7:43. Found: C, 63.72; H, 6.67; N, 7.47.
CIMS (CH$_4$): 341 (100%).
IR(KBr): 3434, 2944, 1663, 1598, 1528, 1496, 1476, 1264 cm$^{-1}$.
$^1$H NMR (d$_6$-DMSO: 10.04, (1H, s), 9.10 (2H, bd) 7.61 (2H, d; J =7.6 Hz), 7.29 (2H, t; J=8.0 Hz), 7.02 (1H, t; J=6.4 Hz), 6.92 (4H, m), 4.63 (1H, m), 4.37 (1H, dd; J=11.6, 2.4 Hz), 4.06 (1H, dd; J=11.6, 6.7 Hz), 3.30 (1H, m), 3.25 (1H, m), 3.01 (2H, bm), 2.37 (2H, t; J=6.7 Hz), 1.68 (4H, bm) ppm.
$^{13}$C NMR (d$_6$-DMSO): 170.79, 142.67, 141.81, 139.27, 128.62, 122.98, 121.71, 119.00, 117.35, 117.12, 69.15, 64.77, 47.17, 46.34, 35.63, 24.89, 22.09 ppm.
Melting Point: 180.5°–181.5° C.

Example 35

5-[(2,3-Dihydro-1,4-benzodioxin-2(S)-yl)methylamino]-N-(4-methoxyphenyl)pentanamide, monohydrochloride Prepared as in Example 19 except using the 5-iodo-N-(4-methoxyphenyl)-pentamide as the alkylating agent and heating at 62° C. for 24 hours. The crude product was chromatographed using 0:10:90 then 3:10:90 diethylamine:ethanol:ethyl acetate. The component with an $R_f$ of ca. 0.50 (in 5:20:80 triethylamine:ethanol:ethyl acetate) was isolated, converted to the hydrochloride salt and recrystallized as in Example 19 to afford a pale yellow solid.

Anal. Calc. for $C_{21}H_{26}N_2O_4 \cdot HCl$: C, 61.98; H, 6.70; N, 6.88. Found: C, 62.00; H, 6.85; N, 6.74.

CIMS (CH$_4$): 371 (100%).

IR(KBr) 3132, 2941, 1658, 1597, 1527, 1518, 1496 cm$^{-1}$.

$^1$H NMR (d$_6$-DMSO): 9.88 (1H, s), 9.20 (1H, bs), 9.00 (1H, bs) 7.51 (2H, d; J=9.1 Hz), 6.90 (6H, m), 4.62 (1H, m), 4.36 (1H, dd; J=11.7, 2.4 Hz), 4.06 (1H, dd; J=11.7, 6.7 Hz), 3.71 (3H, s), 3.33 (1H, bs), 3.20 (1H, m), 3.00 (2H, bs), 2.33 (2H, t; J=6.6 Hz), 1.66 (4H, bm) ppm.

$^{13}$C NMR (d$_6$-DMSO): 170.23, 155.00, 142.68, 141.81, 132.46, 121.73, 120.5, 120.4, 117.4, 117.1, 113.8, 69.2, 64.8, 55.1, 47.2, 46.36, 35.49, 24.92, 22.15 ppm.

Melting point: 198°-199° C.

Example 36

5-[(2,3-Dihydro-1,4-benzodioxin-2-yl)methylamino]-N-(4-fluorophenyl)-pentanamide, monohydrochloride Prepared as in Example 19 except using the 5-iodo-N-(4-fluorophenyl)-pentamide as the alkylating agent and heating at 60° C. for 20 hours. The crude product was chromatographed using 0:10:90 then 3:10:90 diethylamine: ethanol:ethyl acetate. The component with an $R_f$ of ca. 0.50 (in 5:20:80 triethylamine:ethanol:ethyl acetate) was isolated, converted to the hydrochloride salt and recrystallized as in Example 19 to afford a tan solid.

Anal. Calc for $C_{20}H_{23}N_2O_3 \cdot HCl$: C, 60.83; H, 6.14; N, 7:09. Found: C, 60.87; H, 6.32; N, 6.98.

CIMS (CH$_4$): 359 (100%).

IR(KBr): 3294, 2943, 1653, 1510, 1495 cm$^{-1}$.

$^1$H NMR (d$_6$-DMSO): 10.17 (1H, s), 9.35 (1H, bs), 9.12 (1H, bs), 7.64 (2H, dd; J=9.1, 5.1 Hz), 7.13 (2H, t; J=8.9 Hz), 6.89 (4H, m), 4.65 (1H, m), 4.37 (1H, dd; J=11.6, 2.4 Hz), 4.06 (1H, dd; J=11.7, 6.8 Hz), 3.32 (1H, bs), 3.29 (1H, bs), 3.01 (2H, bs), 2.36 (2H, t; J=6.7 Hz), 1.67 (4H, bs) ppm.

$^{13}$C (d$_6$-DMSO): 170.70, 159.37, 156.20, 142.68, 141.83, 135.70, 121.71, 120.74, 120.64, 117.36, 117.12, 115.31, 115.01, 69.15, 64.80, 47.15, 46.34, 35.55, 24.86, 22.10 ppm.

Melting point: 167°-169° C.

Example 37

6-[[2-(5-Hydroxy-1H-indol-3-yl)ethyl]amino]-N-[4-(1-pentyloxy)phenyl]-hexanamide hydrochloride hydrate.

The title comopund was prepared as described in Example 6, with the appropriate reagents to give the desired substitution. The compound was a tan solid.

IR(KBr): 3280, 2956, 2936, 1654, 1540, 1512, 1468, 1238, 832, 801 cm$^{-1}$.

CIMS (CH$_4$): 452 (100%), 305 (34%).

$^1$H NMR (d$_6$-DMSO): 10.66 (1H, bs), 9.83 (1H,S), 8.84 (2H, bs), 8.69 (1H, bs), 7.50 (2H, d; J=9.1 Hz), 7.13-7.10 (2H), 6.87-6.80 (3H), 6.62 (1H, dd; J=2.2, 8.6 Hz), 3.89 (2H, t; J=7.2 Hz), 3.15-3.06 (2H), 3.00-2.89 (4H), 2.30 (2H, t; J=7.4 Hz), 1.70-1.53 (6H), 1.35-1.28 (6H), 0.88 (3H, ; J=6.7 Hz) ppm.

$^{13}$C NMR (d$_6$-DMSO): 170.48, 154.39, 150.38, 132.44, 130.78, 127.46, 123.58, 120.52, 114.31, 111.82, 111.56, 108.35, 102.08, 67.48, 47.03, 46.53, 35.94, 28.43, 27.74, 25.69, 25.32, 24.67, 21.92, 21.81, 13.94, ppm.

What is claimed is:

1. A compound of the formula:

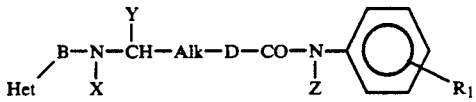

in which B is represented a C$_{1-4}$ alkylene bridging group; Alk is represented by a linear alkylene bridging group containing from 2-8 carbon atoms which may optionally be monosubstituted at any one carbon atoms with a C$_{1-4}$ alkyl, phenyl, substituted phenyl in which said phenyl ring is substituted with up to 3 substituents in which each substituent is independently selected from the group consisting of halogens, C$_{1-4}$ alkyl, C$_{1-4}$ alkoxy, CF$_3$, OCF$_3$, OH, CN, and NO$_2$, or alkylphenyl substituent in which the phenyl ring may be optionally substituted as above; D is represented by a bond or an ethenylene bridging group; X, Y, and Z are each independently represented by hydrogen, C$_{1-4}$ alkyl, phenyl optionally substituted as described above, or alkylphenyl in which the phenyl ring may be optionally substituted as described above; R$_1$ is represented by a substituent selected from the group consisting of hydrogen, halogen, C$_{1-4}$ alkyl, C$_{1-5}$ alkoxy, CF$_3$, OCF$_3$, OH, NO$_2$, CN, —NR$_2$R$_3$, —CONR$_2$R$_3$, —COOR$_4$, —CH$_2$SO$_2$NR$_2$R$_3$, —SO$_2$NR$_2$R$_3$, and —OCH$_2$COOR$_4$; R$_2$ and R$_3$ are each independently represented by H or a C$_{1-4}$ alkyl; R$_4$ is represented by H, C$_{1-4}$ alkyl, phenyl optionally substituted as above, or an alkylphenyl substituent in which the phenyl ring may be optionally substituted as described above; Het is represented by:

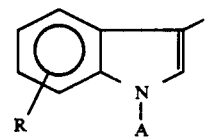

in which R is represented by a substituent selected from the group consisting of hydrogen, halogen, C$_{1-4}$ alkyl, C$_{1-5}$ alkoxy, CF$_3$, OCF$_3$, OH, NO$_2$, CN, —CH$_2$SO$_2$NR$_5$R$_6$, —SO$_2$NR$_5$R$_6$, OCH$_2$C$_6$H$_5$, —CONR$_5$R$_6$, —COOR$_7$ and —OCH$_2$COOR$_7$; R$_5$ and R$_6$ are each independently represented by H or C$_{1-4}$ alkyl; R$_7$ is represented by H, C$_{1-4}$ alkyl, phenyl optionally substituted as above, or an alkylphenyl substituent in which the phenyl ring may be optionally substituted as described above; A is represented by H, or C$_{1-4}$ alkyl; or a pharmaceutically acceptable salt thereof; with the proviso that when Het is an indolyl derivative, then R$_1$ is not a carbonyl derivative.

2. A compound according to claim 1 in which D is a direct bond.

3. A compound according to claim 1 in which B is ethylene

4. A compound according to claim 1 in which R is OH.

5. A compound according to claim 4 in which X is H and B is ethylene.

6. A compound according to claim 5 in which X is H, $CH_3$ or $-CH_2CH_3$.

7. A compound according to claim 6 in which Alk is butylene or pentylene.

8. A compound according to claim 7 in which $R_1$ is a 4-substituent.

9. A compound according to claim 8 in which $R_1$ is $-CF_3$ or $-OCH_3$.

10. A compound according to claim 1 in which said compound is selected from the group consisting of:
6-[[2-(5-hydroxy-1H-indol-3yl)ethyl]amino]-N-[4-(trifluoromethyl)phenyl]-heptanamide,
7-[[2-(5-hydroxy-1H-indol-3-yl)ethyl]amino]-N-(4-methoxyphenyl)-octanamide,
6-[[2-(5-hydroxy-1H-indol-3-yl)ethyl]amino]-N-phenyl-heptanamide,
5-[[2-(5-hydroxy-1H-indol-3-yl)ethyl]amino]-N-[4-(trifluoromethyl)phenyl]-hexanamide,
6-[[2-(5-hydroxy-1H-indol-3-yl)ethyl]amino]-N-(4-methoxyphenyl)-heptanamide,
4-[[2-(5-hydroxy-1H-indol-3-yl)ethyl]amino]-N-[4-(trifluoromethyl)phenyl]-pentanamide,
6-[[2-(5-methoxy-1H-indol-3-yl)ethyl]amino]-N-[4-(trifluoromethyl)phenyl]-heptanamide,
6-[[2-(5-hydroxy-1H-indol-3-yl)ethyl]methylamino]-N-[4-(trifluoromethyl)phenyl]-heptanamide,
6-[[2-(5-hydroxy-1H-indol-3-yl)ethyl]amino]-N-(2-methoxyphenyl)-heptanamide,
6-[[2-(5-carboxamido-1H-indol-3-yl)ethyl]amino]-N-(4-methoxyphenyl)-heptanamide,
6-[[2-(1H-indol-3-yl)ethyl]amino]-N-[4-(trifluoromethyl)phenyl]-hexanamide;
6-[[2-(5-hydroxy-1H-indol-3-yl)ethyl]amino]-N-[4-(1-propyl)phenyl]-hexanamide,
5-[[2-(5-hydroxy-1H-indol-3-yl)ethyl]amino]-N-[4-(1-propyloxy)phenyl]-hexanamide,
7-[[2-(5-hydroxy-1H-indol-3-yl)ethyl]amino]-N-(4-methoxyphenyl)-heptanamide,
7-[[2-(5-hydroxy-1H-indol-3-yl)ethyl]amino]-N-(2-methoxyphenyl)-heptanamide,
6-[[2-(4-hydroxy-1H-indol-3-yl)ethyl]amino]-N-(4-methoxyphenyl)-heptanamide,
6-[[2-(5-chloro-1H-indol-3-yl)ethyl]amino]-N-(4-methoxyphenyl)-heptanamide,
7-[[2-(5-hydroxy-1H-indol-3-yl)ethyl]amino]-N-(3-methoxyphenyl)-octanamide,
6-[[2-(5-hydroxy-1H-indol-3-yl)ethyl]amino]-N-[2-(trifluoromethyl)phenyl]-hexanamide,
6-[[2-(5-hydroxy-1H-indol-3-yl)ethyl]amino]-N-[3-(trifluoromethyl)phenyl]-hexanamide,
6-[[2-(5-hydroxy-1H-indol-3-yl)ethyl]amino]-4-methyl-N-(4-methoxyphenyl)-hexanamide,
6-[[3-(5-hydroxy-1H-indol-3-yl)propyl]amino]-N-(4-methoxyphenyl)-hexanamide,
6-[[2-(5-hydroxy-1H-indol-3-yl)ethyl]amino]-N-(3-methoxyphenyl)-hexanamide,
6-[[2-(5-hydroxy-1-methyl-indol-3-yl)ethyl]amino]-N-(4-methoxyphenyl)-hexanamide, 7-[[2-(5-methoxy-1H-indol-3-yl)ethyl]methylamino]-N-(4-methoxyphenyl)-octanamide,
6-[[2-(5-hydroxy-1H-indol-3-yl)ethyl]amino]-N-(4-methoxyphenyl)-2-hexenamide.

11. A compound according to claim 1 in which said compound is 6-[[2-(5-Hydroxy-1H-indol-3-yl)ethyl]amino]-N-[4-(trifluoromethyl)phenyl]-heptanamide.

12. A compound according to claim 1 in which said compound is 7-[[2-(5-Hydroxy-1H-indol-3-yl)ethyl]amino]-N-(4-methoxyphenyl)-octanamide.

13. A compound according to claim 1 in which said compound is 6-[[2-(5-Hydroxy-1H-indol-3-yl)ethyl]amino]-N-phenyl-heptanamide.

14. A compound according to claim 1 in which said compound is 5-[[2-(5-Hydroxy-1H-indol-3-yl)ethyl]amino]-N-[4-(trifluoromethyl)phenyl]-hexanamide.

15. A compound according to claim 1 in which said compound is 6-[[2-(5-Hydroxy-1H-indol-3-yl)ethyl]amino]-N-(4-methoxyphenyl)-heptanamide.

16. A compound according to claim 1 in which said compound is 6-[[2-(5-Hydroxy-1H-indol-3-yl)ethyl]amino]-N-[4-(trifluoromethyl)phenyl]-hexanamide.

17. A compound according to claim 1 in which said compound is 6-[[2-(5-Hydroxy-1H-indol-3-yl)ethyl]amino]-N-(3,4-dimethoxyphenyl)-heptanamide.

18. A compound according to claim 1 in which said compound is 6-[[2-(5-Hydroxy-1H-indol-3-yl)ethyl]amino]-N-(4-methoxyphenyl)-octanamide.

19. A compound according to claim 1 in which said compound is 4-[[2-(5-Hydroxy-1H-indol-3-yl)ethyl]amino]-N-[4-(trifluoromethyl)phenyl]-pentanamide.

20. A compound according to claim 1 in which said compound is 6-[[2-(5-Hydroxy-1H-indol-3-yl)ethyl]amino]-N-(2-methoxyphenyl)-heptanamide.

21. A compound according to claim 1 in which said compound is 7-[2-(5-hydroxy-1H-indol-3-yl)ethyl]amino]-N-phenyl-heptanamide.

22. A compound according to claim 1 in which said compound is 6-[[2-(5-hydroxy-1H-indol-3-yl)ethyl]amino]-N-[3-(trifluoromethyl)phenyl]-hexanamide.

23. A compound according to claim 1 in which said compound is 6-[[2-(5-Hydroxy-1H-indol-3-yl)ethyl]amino]-N-[4-(trifluoromethyl)phenyl]-hexanamide.

24. A composition comprising a compound according to claim 1 in admixture with an inert carrier.

25. A composition according to claim 7 wherein said composition is a pharmaceutical composition.

* * * * *